(12) United States Patent
Rothbauer et al.

(10) Patent No.: US 8,999,669 B2
(45) Date of Patent: Apr. 7, 2015

(54) DETECTION AND VISUALIZATION OF THE CELL CYCLE IN LIVING CELLS

(75) Inventors: Ulrich Rothbauer, Tuebingen (DE); Heinrich Leonhardt, Munich (DE); Kourosh Zolghadr, Munich (DE); Tina Romer, Munich (DE); Katrin Schmidthals, Munich (DE)

(73) Assignee: Ludwig-Maximilians Universitat München, Munich (DE)

( * ) Notice: Subject to any disclaimer, the term of this patent is extended or adjusted under 35 U.S.C. 154(b) by 184 days.

(21) Appl. No.: 13/382,302

(22) PCT Filed: Jul. 6, 2010

(86) PCT No.: PCT/EP2010/059622
§ 371 (c)(1),
(2), (4) Date: Feb. 27, 2012

(87) PCT Pub. No.: WO2011/003896
PCT Pub. Date: Jan. 13, 2011

(65) Prior Publication Data
US 2012/0149028 A1    Jun. 14, 2012

(30) Foreign Application Priority Data
Jul. 6, 2009 (EP) .................... 09008827

(51) Int. Cl.
*C12P 21/06* (2006.01)
*C07K 16/18* (2006.01)
*G01N 33/58* (2006.01)
*G01N 33/68* (2006.01)

(52) U.S. Cl.
CPC .............. *C07K 16/18* (2013.01); *G01N 33/582* (2013.01); *G01N 33/6875* (2013.01); *C07K 2317/22* (2013.01); *C07K 2319/60* (2013.01); *G01N 2500/10* (2013.01)

(58) Field of Classification Search
None
See application file for complete search history.

(56) References Cited

FOREIGN PATENT DOCUMENTS

| EP | 2055718 | 5/2009 |
|---|---|---|
| WO | WO 2007/134350 A2 * | 11/2007 |
| WO | 2009/080764 | 7/2009 |

OTHER PUBLICATIONS

Greenspan et al (Nature Biotechnology 7: 936-937, 1999).*
Chothia et al (The EMBO Journal, 1986, 5/4:823-26.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Rottach Andrea et al. "Generation and characterization of a rat monoclonal antibody specific for PCNA" Hybridoma, vol. 27, No. 2, Apr. 2008, p. 91, XP002553545.
Rothbauer Ulrich, et al. "Targeting and tracing antigens in live cells with fluorescent nanobodies" Nature Methods, vol. 3, No. 11, Nov. 2006, pp. 887-889, XP002553544.
PCT International Search Report dated Oct. 19, 2010 for International Application No. PCT/EP2010/059622.

* cited by examiner

*Primary Examiner* — Jennifer Graser
(74) *Attorney, Agent, or Firm* — Donna T. Ward; Heng Zhu; DT Ward, P.C.

(57) ABSTRACT

The present invention relates to a nucleic acid molecule encoding a polypeptide specifically binding to proliferating cell nuclear antigen (PCNA). The present invention also relates to a vector comprising the nucleic acid molecule of the invention, a host cell comprising the nucleic acid molecule of or the vector of the invention and a method of detecting the amount and/or location of PCNA in living cells, a method of screening for compounds having an effect on the cell cycle.

16 Claims, 12 Drawing Sheets

Figure 2:
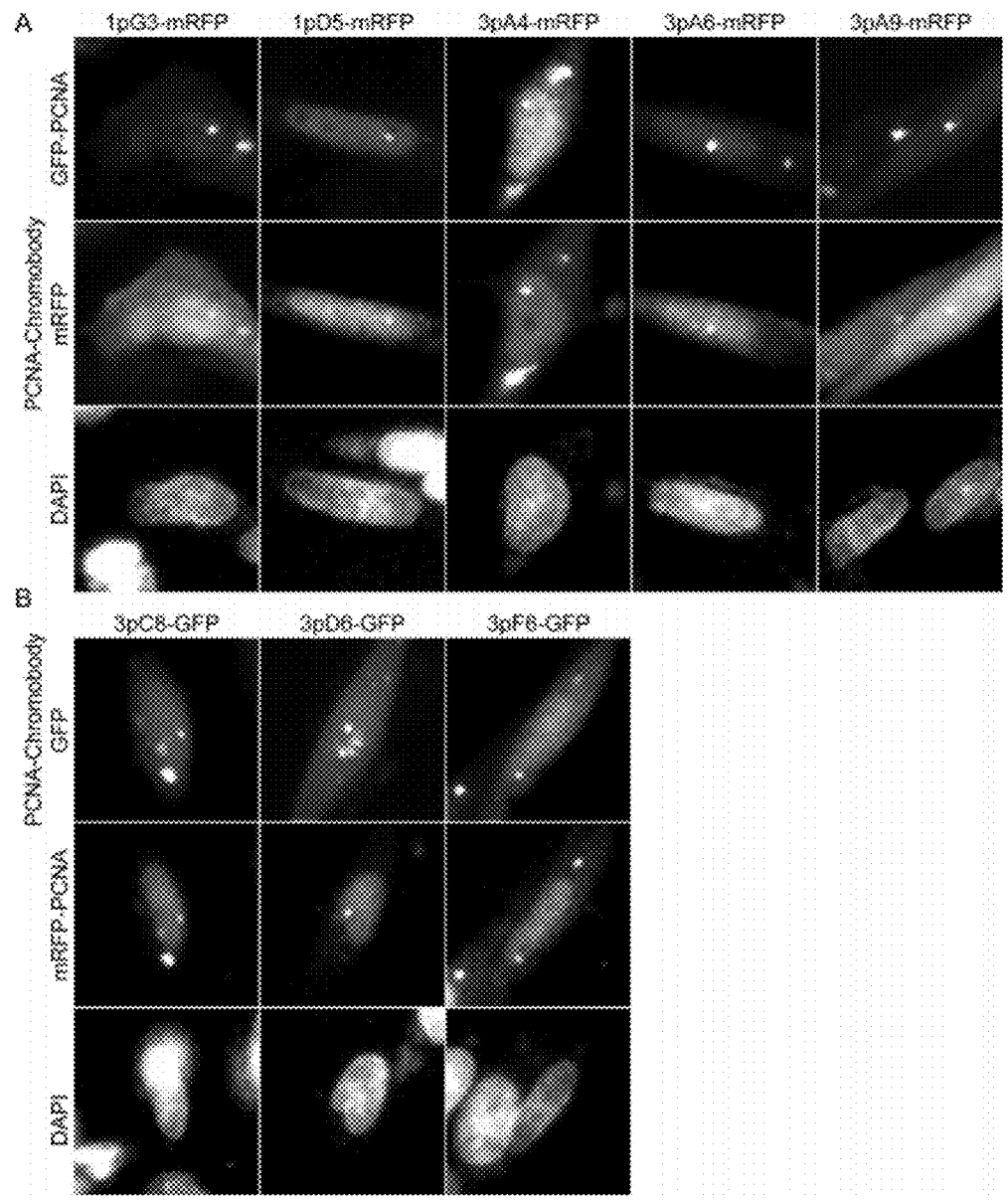

Alignment of polypeptides of the invention specifically binding to PCNA

SEQUENCE LISTING

```
<160> NUMBER OF SEQ ID NOS: 41

<210> SEQ ID NO 1
<211> LENGTH: 368
<212> TYPE: DNA
<213> ORGANISM: Lamos pacos

<400> SEQUENCE: 1
atggctcagg tgcagctggt ggagtctggg ggaggcttgg tgcaacctgg ggggtctctg      60
agactctcct gtgcagcctc tggattcacc ttcagtagct atgctatgag ctgggtccgc     120
caggctccag gaaaggggct cgagtgggtc tcagatatta gtcctagtgg tgctgtcaag     180
gcctattcag actccgtgaa gggccggttc accatctcca gagacaacgc caagaacaga     240
ctgtatctgc aaatgaacag cctgacacct gaggacacgg gcgaatattt ttgtactaaa     300
gtccagtccc cacgtacgag aatacctgcc ccctcgagcc aggggaccca ggtcaccgtc     360
```

```
tcctcaag                                                         368
```

```
<210> SEQ ID NO 2
<211> LENGTH: 122
<212> TYPE: PRT
<213> ORGANISM: Lamos pacos

<400> SEQUENCE: 2
```

```
Met Ala Gln Val Gln Leu Val Glu Ser Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
                35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120
```

```
<210> SEQ ID NO 3
<211> LENGTH: 717
<212> TYPE: DNA
<213> ORGANISM: Aequorea Victoria

<400> SEQUENCE: 3
```

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcaagat acccagatca tatgaaacag   240
catgactttt tcaagagtgc catgcccgaa ggttatgtac aggaaagaac tatattttc    300
aaagatgacg ggaactacaa gacacgtgct gaagtcaagt ttgaaggtga tacccttgtt   360
aatagaatcg agttaaaagg tattgatttt aagaagatg gaaacattct tggacacaaa    420
ttggaataca actataactc acacaatgta tacatcatgg cagacaaaca aaagaatgga   480
atcaaagtta acttcaaaat tagacacaac attgaagatg aagcgttca actagcagac     540
cattatcaac aaaatactcc aattggcgat ggccctgtcc ttttaccaga caaccattac   600
ctgtccacac aatctgccct ttcgaaagat cccaacgaaa agagagacca catggtcctt   660
cttgagtttg taacagctgc tgggattaca catggcatgg atgaactata caaataa       717
```

```
<210> SEQ ID NO 4
<211> LENGTH: 238
<212> TYPE: PRT
<213> ORGANISM: Aequorea Victoria

<400> SEQUENCE: 4
```

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30
```

Gly Glu Gly Asp Ala Thr Tyr Gly Lys Leu Thr Leu Lys Phe Ile Cys
          35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
             100                 105                 110

Lys Phe Glu Gly Asp Thr Leu Val Asn Arg Ile Glu Leu Lys Gly Ile
         115                 120                 125

Asp Phe Lys Glu Asp Gly Asn Ile Leu Gly His Lys Leu Glu Tyr Asn
     130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 711
<212> TYPE: DNA
<213> ORGANISM: Artificial sequence
<220> FEATURE:
<223> OTHER INFORMATION: /note="Description of artificial sequence:
      mCherry"

<400> SEQUENCE: 5
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420 atgcagaaga gaccatgggc tgggaggcc tcctccgagc ggatgtaccc cgaggacggc      480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagta a              711

<210> SEQ ID NO 6
<211> LENGTH: 236
<212> TYPE: PRT

<213> ORGANISM: Artificial sequence
<220> FEATURE:
<223> OTHER INFORMATION: /note="Description of artificial sequence: mCherry"

<400> SEQUENCE: 6

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 7
<211> LENGTH: 759
<212> TYPE: DNA
<213> ORGANISM: Artificial sequence
<220> FEATURE:
<223> OTHER INFORMATION: /note="Description of artificial sequence: YFP"

<400> SEQUENCE: 7

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgaag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
```

```
gaccactacc agcagaacac ccccatcggc gacggccccg tgctgctgcc cgacaaccac    600
tacctgagct accagtccaa gctgagcaaa gaccccaacg agaagcgcga tcacatggtc    660
ctgctggagt tcgtgaccgc cgccgggatc actctcggca tggacgagct gtacaaggct    720
ggtaccgagc tcggatccac tagtaacggc cgccagtgt                           759
```

<210> SEQ ID NO 8
<211> LENGTH: 239
<212> TYPE: PRT
<213> ORGANISM: Artificial sequence
<220> FEATURE:
<223> OTHER INFORMATION: /note="Description of artificial sequence: YFP"

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 9
<211> LENGTH: 1149
<212> TYPE: DNA
<213> ORGANISM: Artificial sequence
<220> FEATURE:
<223> OTHER INFORMATION: /note="Description of artificial sequence:
    PCNA3p16-GFP (including linker)"

<400> SEQUENCE: 9

```
atggctcagg tgcagctggt ggagtctggg ggaggcttgg tgcaacctgg ggggtctctg     60
agactctcct gtgcagcctc tggattcacc ttcagtagct atgctatgag ctgggtccgc    120
```

| | |
|---|---|
| caggctccag gaaaggggct cgagtgggtc tcagatatta gtcctagtgg tgctgtcaag | 180 |
| gcctattcag actccgtgaa gggccggttc accatctcca gagacaacgc caagaacaga | 240 |
| ctgtatctgc aaatgaacag cctgacacct gaggacacgg gcgaatattt ttgtactaaa | 300 |
| gtccagtccc cacgtacgag aatacctgcc ccctcgagcc aggggaccca ggtcaccgtc | 360 |
| tcctcaagaa gcttcgaatt ctgcagtcga cggtaccgcg ggcccgggat ccaccggccg | 420 |
| gtcgccacca tggtgagcaa gggcgaggag ctgttcaccg gggtggtgcc catcctggtc | 480 |
| gagctggacg gcgacgtaaa cggccacaag ttcagcgtgt ccggcgaggg cgagggcgat | 540 |
| gccacctacg gcaagctgac cctgaagttc atctgcacca ccggcaagct gcccgtgccc | 600 |
| tggcccaccc tcgtgaccac cctgacctac ggcgtgcagt gcttcagccg ctaccccgac | 660 |
| cacatgaagc agcacgactt cttcaagtcc gccatgcccg aaggctacgt ccaggagcgc | 720 |
| accatcttct tcaaggacga cggcaactac aagacccgcg ccgaggtgaa gttcgagggc | 780 |
| gacaccctgg tgaaccgcat cgagctgaag ggcatcgact tcaaggagga cggcaacatc | 840 |
| ctggggcaca gctggagta caactacaac agccacaacg tctatatcat ggccgacaag | 900 |
| cagaagaacg gcatcaaggt gaacttcaag atccgccaca acatcgagga cggcagcgtg | 960 |
| cagctcgccg accactacca gcagaacacc cccatcggcg acggccccgt gctgctgccc | 1020 |
| gacaaccact acctgagcac ccagtccgcc ctgagcaaag accccaacga gaagcgcgat | 1080 |
| cacatggtcc tgctggagtt cgtgaccgcc gccgggatca ctctcggcat ggacgagctg | 1140 |
| tacaagtaa | 1149 |

<210> SEQ ID NO 10
<211> LENGTH: 382
<212> TYPE: PRT
<213> ORGANISM: Artificial sequence
<220> FEATURE:
<223> OTHER INFORMATION: /note="Description of artificial sequence: PCNA3p16-GFP (including linker)"

<400> SEQUENCE: 10

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser Arg Ser Phe Glu Phe Cys
        115                 120                 125

Ser Arg Arg Tyr Arg Gly Pro Gly Ile His Arg Pro Val Ala Thr Met
    130                 135                 140

Val Ser Lys Gly Glu Glu Leu Phe Thr Gly Val Val Pro Ile Leu Val
145                 150                 155                 160

Glu Leu Asp Gly Asp Val Asn Gly His Lys Phe Ser Val Ser Gly Glu
                165                 170                 175

```
Gly Glu Gly Asp Ala Thr Tyr Gly Lys Leu Thr Leu Lys Phe Ile Cys
            180                 185                 190
Thr Thr Gly Lys Leu Pro Val Pro Trp Pro Thr Leu Val Thr Thr Leu
        195                 200                 205
Thr Tyr Gly Val Gln Cys Phe Ser Arg Tyr Pro Asp His Met Lys Gln
    210                 215                 220
His Asp Phe Phe Lys Ser Ala Met Pro Glu Gly Tyr Val Gln Glu Arg
225                 230                 235                 240
Thr Ile Phe Phe Lys Asp Asp Gly Asn Tyr Lys Thr Arg Ala Glu Val
                245                 250                 255
Lys Phe Glu Gly Asp Thr Leu Val Asn Arg Ile Glu Leu Lys Gly Ile
            260                 265                 270
Asp Phe Lys Glu Asp Gly Asn Ile Leu Gly His Lys Leu Glu Tyr Asn
        275                 280                 285
Tyr Asn Ser His Asn Val Tyr Ile Met Ala Asp Lys Gln Lys Asn Gly
    290                 295                 300
Ile Lys Val Asn Phe Lys Ile Arg His Asn Ile Glu Asp Gly Ser Val
305                 310                 315                 320
Gln Leu Ala Asp His Tyr Gln Gln Asn Thr Pro Ile Gly Asp Gly Pro
                325                 330                 335
Val Leu Leu Pro Asp Asn His Tyr Leu Ser Thr Gln Ser Ala Leu Ser
            340                 345                 350
Lys Asp Pro Asn Glu Lys Arg Asp His Met Val Leu Leu Glu Phe Val
        355                 360                 365
Thr Ala Ala Gly Ile Thr Leu Gly Met Asp Glu Leu Tyr Lys
    370                 375                 380
```

<210> SEQ ID NO 11
<211> LENGTH: 1140
<212> TYPE: DNA
<213> ORGANISM: Artificial sequence
<220> FEATURE:
<223> OTHER INFORMATION: /note="Description of artificial sequence: PCNA3p16-mCherry (including linker)"

<400> SEQUENCE: 11

```
atggctcagg tgcagctggt ggagtctggg ggaggcttgg tgcaacctgg ggggtctctg      60
agactctcct gtgcagcctc tggattcacc ttcagtagct atgctatgag ctgggtccgc     120
caggctccag gaaagggct cgagtgggtc tcagatatta gtcctagtgg tgctgtcaag     180
gcctattcag actccgtgaa gggccggttc accatctcca gagacaacgc caagaacaga     240
ctgtatctgc aaatgaacag cctgacacct gaggacacgg cgaatatttt tgtactaaa      300
gtccagtccc cacgtacgag aatacctgcc ccctcgagcc agggacccca ggtcaccgtc     360
tcctcaagaa gcttcgaatt ctgcagtcga cggtaccgcg ggcccgggat ccaccggccg     420
gtcgccacca tggtgagcaa gggcgaggag gataacatgg ccatcatcaa ggagttcatg     480
cgcttcaagg tgcacatgga gggctccgtg aacggccacg agttcgagat cgagggcgag     540
ggcgagggcc gcccctacga gggcacccag accgccaagc tgaaggtgac caagggtggc     600
cccctgccct cgcctggga catcctgtcc cctcagttca tgtacggctc caaggcctac     660
gtgaagcacc ccgccgacat ccccgactac ttgaagctgt ccttccccga gggcttcaag     720
tgggagcgcg tgatgaactt cgaggacggc ggcgtggtga ccgtgaccca ggactcctcc     780
ctgcaggacg gcgagttcat ctacaaggtg aagctgcgcg gcaccaactt ccctccggac     840
```

```
ggccccgtaa tgcagaagaa gaccatgggc tgggaggcct cctccgagcg gatgtacccc    900
gaggacggcg ccctgaaggg cgagatcaag cagaggctga agctgaagga cggcggccac    960
tacgacgctg aggtcaagac cacctacaag gccaagaagc ccgtgcagct gcccggcgcc   1020
tacaacgtca acatcaagtt ggacatcacc tcccacaacg aggactacac catcgtggaa   1080
cagtacgaac gcgccgaggg ccgccactcc accggcggca tggacgagct gtacaagtaa   1140
```

<210> SEQ ID NO 12
<211> LENGTH: 379
<212> TYPE: PRT
<213> ORGANISM: Artificial sequence
<220> FEATURE:
<223> OTHER INFORMATION: /note="Description of artificial sequence:
      PCNA3p16-mCherry (including linker)"

<400> SEQUENCE: 12

```
Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser Arg Ser Phe Glu Phe Cys
        115                 120                 125

Ser Arg Arg Tyr Arg Gly Pro Gly Ile His Arg Pro Val Ala Thr Met
    130                 135                 140

Val Ser Lys Gly Glu Glu Asp Asn Met Ala Ile Ile Lys Glu Phe Met
145                 150                 155                 160

Arg Phe Lys Val His Met Glu Gly Ser Val Asn Gly His Glu Phe Glu
                165                 170                 175

Ile Glu Gly Glu Gly Glu Gly Arg Pro Tyr Glu Gly Thr Gln Thr Ala
            180                 185                 190

Lys Leu Lys Val Thr Lys Gly Gly Pro Leu Pro Phe Ala Trp Asp Ile
        195                 200                 205

Leu Ser Pro Gln Phe Met Tyr Gly Ser Lys Ala Tyr Val Lys His Pro
    210                 215                 220

Ala Asp Ile Pro Asp Tyr Leu Lys Leu Ser Phe Pro Glu Gly Phe Lys
225                 230                 235                 240

Trp Glu Arg Val Met Asn Phe Glu Asp Gly Gly Val Val Thr Val Thr
                245                 250                 255

Gln Asp Ser Ser Leu Gln Asp Gly Glu Phe Ile Tyr Lys Val Lys Leu
            260                 265                 270

Arg Gly Thr Asn Phe Pro Ser Asp Gly Pro Val Met Gln Lys Lys Thr
        275                 280                 285

Met Gly Trp Glu Ala Ser Ser Glu Arg Met Tyr Pro Glu Asp Gly Ala
    290                 295                 300

Leu Lys Gly Glu Ile Lys Gln Arg Leu Lys Leu Lys Asp Gly Gly His
```

```
                305                 310                 315                 320
Tyr Asp Ala Glu Val Lys Thr Thr Tyr Lys Ala Lys Lys Pro Val Gln
                    325                 330                 335
Leu Pro Gly Ala Tyr Asn Val Asn Ile Lys Leu Asp Ile Thr Ser His
                340                 345                 350
Asn Glu Asp Tyr Thr Ile Val Glu Gln Tyr Glu Arg Ala Glu Gly Arg
                355                 360                 365
His Ser Thr Gly Gly Met Asp Glu Leu Tyr Lys
            370                 375

<210> SEQ ID NO 13
<211> LENGTH: 21
<212> TYPE: PRT
<213> ORGANISM: Artificial sequence
<220> FEATURE:
<223> OTHER INFORMATION: /note="Description of artificial sequence:
      linker peptide"

<400> SEQUENCE: 13

Arg Ser Phe Glu Phe Cys Ser Arg Arg Tyr Arg Gly Pro Gly Ile His
1               5                   10                  15
Arg Pro Val Ala Thr
            20

<210> SEQ ID NO 14
<211> LENGTH: 20
<212> TYPE: PRT
<213> ORGANISM: Artificial sequence
<220> FEATURE:
<223> OTHER INFORMATION: /note="Description of artificial sequence:
      linker peptide"

<400> SEQUENCE: 14

Ser Arg Ser Leu Ser Ile Pro Ser Thr Val Pro Arg Ala Arg Asp Pro
1               5                   10                  15
Pro Val Asp Met
            20

<210> SEQ ID NO 15
<211> LENGTH: 366
<212> TYPE: DNA
<213> ORGANISM: Lamos pacos

<400> SEQUENCE: 15
atggctaacg tgcagctgaa tgagtctggg ggaggcttgg tgcaacctgg ggggtctctg      60
agactctcct gtgcagcctc tggattcacc ttcagtagct atgctatgag ctgggtccgc     120
caggctccag gaaaggggct cgagtgggtc tcagatatta gtcctagtgg tgctgtcaag     180
gcctattcag actccgtgaa gggccggttc accatctcca gagacaacgc caagaacaga     240
ctgtatctgc aaatgaacag cctgacacct gaggacacgg cgaatatttt tgtactaaa      300 gtccagtccc cacgtacgag aatacctgcc ccctcgagcc aggggaccca ggtcaccgtc     360
tcctca                                                                366

<210> SEQ ID NO 16
<211> LENGTH: 122
<212> TYPE: PRT
<213> ORGANISM: Lamos pacos

<400> SEQUENCE: 16

Met Ala Asn Val Gln Leu Asn Glu Ser Gly Gly Gly Leu Val Gln Pro
```

```
            1               5              10              15
Gly Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu Glu
            35                  40                  45

Trp Val Ser Asp Ile Ser Pro Ser Gly Ala Val Lys Ala Tyr Ser Asp
        50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
                100                 105                 110

Ser Gln Gly Thr Gln Val Thr Val Ser Ser
            115                 120
```

<210> SEQ ID NO 17
<211> LENGTH: 366
<212> TYPE: DNA
<213> ORGANISM: Lamos pacos

<400> SEQUENCE: 17

```
atggctaacg tgcagctgaa tgagtctggg ggaggcttgg tgcaacctgg ggggtctctg      60
agactctcct gtgcagcctc tggattcacc ttcagttcgt atgctatgag ttgggtccgc     120
caggctccag gaaaggggct cgagtgggtc tccgagatta gtcctagtgg tgctgtcaag     180
gcctattcag actccgtgaa gggccggttc accatctcca gagacaacgc caagaacaga     240
ctgtatctgc aaatgaacag cctgacacct gaggacacgg gcgaatattt ttgtactaaa     300
gtccagtccc cacgtacgag aatacctgcc ccctcgagcc aggggaccca ggtcaccgtc     360
tcctca                                                               366
```

<210> SEQ ID NO 18
<211> LENGTH: 122
<212> TYPE: PRT
<213> ORGANISM: Lamos pacos

<400> SEQUENCE: 18

```
Met Ala Asn Val Gln Leu Asn Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
            35                  40                  45

Trp Val Ser Glu Ile Ser Pro Ser Gly Ala Val Lys Ala Tyr Ser Asp
        50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
                100                 105                 110

Ser Gln Gly Thr Gln Val Thr Val Ser Ser
            115                 120
```

<210> SEQ ID NO 19

<211> LENGTH: 1149
<212> TYPE: DNA
<213> ORGANISM: Artificial sequence
<220> FEATURE:
<223> OTHER INFORMATION: /note="Description of artificial sequence: nucleic acid encoding binder of SEQ ID NO: 16 fused to GFP (including linker)"

<400> SEQUENCE: 19

```
atggctaacg tgcagctgaa tgagtctggg ggaggcttgg tgcaacctgg ggggtctctg      60
agactctcct gtgcagcctc tggattcacc ttcagtagct atgctatgag ctgggtccgc     120
caggctccag aaaggggct cgagtgggtc tcagatatta gtcctagtgg tgctgtcaag     180
gcctattcag actccgtgaa gggccggttc accatctcca gagacaacgc caagaacaga     240
ctgtatctgc aaatgaacag cctgacacct gaggacacgg cgaatatttt ttgtactaaa     300
gtccagtccc cacgtacgag aatacctgcc ccctcgagcc agggacccca ggtcaccgtc     360
tcctcaagaa gcttcgaatt ctgcagtcga cggtaccgcg ggcccgggat ccaccggccg     420
gtcgccacca tggtgagcaa gggcgaggag ctgttcaccg gggtggtgcc catcctggtc     480
gagctggacg gcgacgtaaa cggccacaag ttcagcgtgt ccggcgaggg cgagggcgat     540
gccacctacg gcaagctgac cctgaagttc atctgcacca ccggcaagct gcccgtgccc     600
tggcccaccc tcgtgaccac cctgacctac ggcgtgcagt gcttcagccg ctaccccgac     660
cacatgaagc agcacgactt cttcaagtcc gccatgcccg aaggctacgt ccaggagcgc     720
accatcttct tcaaggacga cggcaactac aagacccgcg ccgaggtgaa gttcgagggc     780
gacaccctgg tgaaccgcat cgagctgaag ggcatcgact tcaaggagga cggcaacatc     840
ctggggcaca gctggagta caactacaac agccacaacg tctatatcat ggccgacaag     900
cagaagaacg gcatcaaggt gaacttcaag atccgccaca acatcgagga cggcagcgtg     960
cagctcgccg accactacca gcagaacacc cccatcggcg acggccccgt gctgctgccc    1020
gacaaccact acctgagcac ccagtccgcc ctgagcaaag accccaacga gaagcgcgat    1080
cacatggtcc tgctggagtt cgtgaccgcc gccgggatca ctctcggcat ggacgagctg    1140
tacaagtaa                                                            1149
```

<210> SEQ ID NO 20
<211> LENGTH: 382
<212> TYPE: PRT
<213> ORGANISM: Artificial sequence
<220> FEATURE:
<223> OTHER INFORMATION: /note="Description of artificial sequence: binder of SEQ ID NO: 16 fused to GFP (including linker)"

<400> SEQUENCE: 20

```
Met Ala Asn Val Gln Leu Asn Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95
```

Phe Cys Thr Lys Val Gln Ser Pro Arg Thr Arg Ile Pro Ala Pro Ser
            100                 105                 110

Ser Gln Gly Thr Gln Val Thr Val Ser Ser Arg Ser Phe Glu Phe Cys
        115                 120                 125

Ser Arg Arg Tyr Arg Gly Pro Gly Ile His Arg Pro Val Ala Thr Met
    130                 135                 140

Val Ser Lys Gly Glu Glu Leu Phe Thr Gly Val Val Pro Ile Leu Val
145                 150                 155                 160

Glu Leu Asp Gly Asp Val Asn Gly His Lys Phe Ser Val Ser Gly Glu
                165                 170                 175

Gly Glu Gly Asp Ala Thr Tyr Gly Lys Leu Thr Leu Lys Phe Ile Cys
            180                 185                 190

Thr Thr Gly Lys Leu Pro Val Pro Trp Pro Thr Leu Val Thr Thr Leu
        195                 200                 205

Thr Tyr Gly Val Gln Cys Phe Ser Arg Tyr Pro Asp His Met Lys Gln
    210                 215                 220

His Asp Phe Phe Lys Ser Ala Met Pro Glu Gly Tyr Val Gln Glu Arg
225                 230                 235                 240

Thr Ile Phe Phe Lys Asp Asp Gly Asn Tyr Lys Thr Arg Ala Glu Val
                245                 250                 255

Lys Phe Glu Gly Asp Thr Leu Val Asn Arg Ile Glu Leu Lys Gly Ile
            260                 265                 270

Asp Phe Lys Glu Asp Gly Asn Ile Leu Gly His Lys Leu Glu Tyr Asn
        275                 280                 285

Tyr Asn Ser His Asn Val Tyr Ile Met Ala Asp Lys Gln Lys Asn Gly
    290                 295                 300

Ile Lys Val Asn Phe Lys Ile Arg His Asn Ile Glu Asp Gly Ser Val
305                 310                 315                 320

Gln Leu Ala Asp His Tyr Gln Gln Asn Thr Pro Ile Gly Asp Gly Pro
                325                 330                 335

Val Leu Leu Pro Asp Asn His Tyr Leu Ser Thr Gln Ser Ala Leu Ser
            340                 345                 350

Lys Asp Pro Asn Glu Lys Arg Asp His Met Val Leu Leu Glu Phe Val
        355                 360                 365

Thr Ala Ala Gly Ile Thr Leu Gly Met Asp Glu Leu Tyr Lys
    370                 375                 380

<210> SEQ ID NO 21
<211> LENGTH: 1149
<212> TYPE: DNA
<213> ORGANISM: Artificial sequence
<220> FEATURE:
<223> OTHER INFORMATION: /note="Description of artificial sequence:
      nucleic acid encoding binder of SEQ ID NO: 18 fused to GFP
      (including linker)"

<400> SEQUENCE: 21
atggctaacg tgcagctgaa tgagtctggg ggaggcttgg tgcaacctgg ggggtctctg      60
agactctcct gtgcagcctc tggattcacc ttcagttcgt atgctatgag ttgggtccgc     120
caggctccag gaaaggggct cgagtgggtc tccgagatta gtcctagtgg tgctgtcaag     180
gcctattcag actccgtgaa gggccggttc accatctcca gagacaacgc caagaacaga     240
ctgtatctgc aaatgaacag cctgacacct gaggacacgg cgaatatttt tgtactaaa      300 gtccagtccc cacgtacgag aatacctgcc cctcgagcc aggggaccca ggtcaccgtc     360
tcctcaagaa gcttcgaatt ctgcagtcga cggtaccgcg ggcccgggat ccaccggccg     420

```
gtcgccacca tggtgagcaa gggcgaggag ctgttcaccg gggtggtgcc catcctggtc    480
gagctggacg gcgacgtaaa cggccacaag ttcagcgtgt ccggcgaggg cgagggcgat    540
gccacctacg gcaagctgac cctgaagttc atctgcacca ccggcaagct gcccgtgccc    600
tggcccaccc tcgtgaccac cctgacctac ggcgtgcagt gcttcagccg ctaccccgac    660
cacatgaagc agcacgactt cttcaagtcc gccatgcccg aaggctacgt ccaggagcgc    720
accatcttct caaggacga cggcaactac aagacccgcg ccgaggtgaa gttcgagggc    780
gacaccctgg tgaaccgcat cgagctgaag ggcatcgact tcaaggagga cggcaacatc    840
ctggggcaca gcctggagta caactacaac agccacaacg tctatatcat ggccgacaag    900
cagaagaacg gcatcaaggt gaacttcaag atccgccaca acatcgagga cggcagcgtg    960
cagctcgccg accactacca gcagaacacc cccatcggcg acggccccgt gctgctgccc    1020
gacaaccact acctgagcac ccagtccgcc ctgagcaaag accccaacga aaagcgcgat    1080
cacatggtcc tgctggagtt cgtgaccgcc gccgggatca ctctcggcat ggacgagctg    1140
tacaagtaa                                                            1149
```

<210> SEQ ID NO 22
<211> LENGTH: 382
<212> TYPE: PRT
<213> ORGANISM: Artificial sequence
<220> FEATURE:
<223> OTHER INFORMATION: /note="Description of artificial sequence: binder of SEQ ID NO: 18 fused to GFP (including linker)"

<400> SEQUENCE: 22

```
Met Ala Asn Val Gln Leu Asn Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Glu Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser Arg Ser Phe Glu Phe Cys
        115                 120                 125

Ser Arg Arg Tyr Arg Gly Pro Gly Ile His Arg Pro Val Ala Thr Met
    130                 135                 140

Val Ser Lys Gly Glu Glu Leu Phe Thr Gly Val Val Pro Ile Leu Val
145                 150                 155                 160

Glu Leu Asp Gly Asp Val Asn Gly His Lys Phe Ser Val Ser Gly Glu
                165                 170                 175

Gly Glu Gly Asp Ala Thr Tyr Gly Lys Leu Thr Leu Lys Phe Ile Cys
            180                 185                 190

Thr Thr Gly Lys Leu Pro Val Pro Trp Pro Thr Leu Val Thr Thr Leu
        195                 200                 205

Thr Tyr Gly Val Gln Cys Phe Ser Arg Tyr Pro Asp His Met Lys Gln
    210                 215                 220
```

```
His Asp Phe Phe Lys Ser Ala Met Pro Glu Gly Tyr Val Gln Glu Arg
225                 230                 235                 240

Thr Ile Phe Phe Lys Asp Asp Gly Asn Tyr Lys Thr Arg Ala Glu Val
            245                 250                 255

Lys Phe Glu Gly Asp Thr Leu Val Asn Arg Ile Glu Leu Lys Gly Ile
        260                 265                 270

Asp Phe Lys Glu Asp Gly Asn Ile Leu Gly His Lys Leu Glu Tyr Asn
    275                 280                 285

Tyr Asn Ser His Asn Val Tyr Ile Met Ala Asp Lys Gln Lys Asn Gly
290                 295                 300

Ile Lys Val Asn Phe Lys Ile Arg His Asn Ile Glu Asp Gly Ser Val
305                 310                 315                 320

Gln Leu Ala Asp His Tyr Gln Gln Asn Thr Pro Ile Gly Asp Gly Pro
            325                 330                 335

Val Leu Leu Pro Asp Asn His Tyr Leu Ser Thr Gln Ser Ala Leu Ser
        340                 345                 350

Lys Asp Pro Asn Glu Lys Arg Asp His Met Val Leu Leu Glu Phe Val
    355                 360                 365

Thr Ala Ala Gly Ile Thr Leu Gly Met Asp Glu Leu Tyr Lys
        370                 375                 380

<210> SEQ ID NO 23
<211> LENGTH: 120
<212> TYPE: PRT
<213> ORGANISM: Lamos pacos

<400> SEQUENCE: 23

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Gly Leu Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Ala Val Tyr
                85                  90                  95

Tyr Cys Ala Asn Arg Gly Leu Gly Val Asn Lys Leu Leu Arg Gly Gln
            100                 105                 110

Gly Thr Gln Val Thr Val Ser Ser
        115                 120

<210> SEQ ID NO 24
<211> LENGTH: 131
<212> TYPE: PRT
<213> ORGANISM: Lamos pacos

<400> SEQUENCE: 24

Met Ala Gln Val Gln Leu Val Glu Ser Gly Gly Gly Ser Val Arg Ala
1               5                   10                  15

Gly Asp Ser Leu Arg Leu Ser Cys Ala Ser Ser Gly Arg Thr Phe Pro
            20                  25                  30

Gly Pro Asn Met Ala Trp Phe Arg Gly Gly Pro Gly Gln Glu Arg Glu
        35                  40                  45
```

```
Phe Val Ala Ala Ile Thr Ser Arg Asp Ser Lys Thr Tyr Tyr Ala Asp
    50                  55                  60

Ser Ala Lys Gly Arg Phe Thr Ile Ser Arg Asp Asn Ala Lys Arg Thr
65                  70                  75                  80

Val Tyr Leu Gln Met Asn Asn Leu Lys Pro Glu Asp Thr Ala Val Tyr
                    85                  90                  95

Tyr Cys Val Ala Leu Arg Phe Ile Gly Gly Val Cys Pro Lys Val Val
                100                 105                 110

Leu Thr Gln Arg Pro Ser Asp Tyr Arg Gly Gln Gly Thr Gln Val Thr
                115                 120                 125

Val Ser Ser
    130
```

```
<210> SEQ ID NO 25
<211> LENGTH: 122
<212> TYPE: PRT
<213> ORGANISM: Lamos pacos

<400> SEQUENCE: 25

Met Ala Gln Val Gln Leu Val Glu Ser Gly Gly Gly Leu Val Arg Pro
1               5                   10                  15

Gly Gly Ser Leu Thr Leu Ser Cys Ala Ala Ser Gly Phe Thr Phe Ser
                20                  25                  30

Ser Tyr Gly Leu Ser Trp Val Arg Gln Ala Pro Gly Lys Gly Leu Glu
            35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
                100                 105                 110

Ser Gln Gly Thr Gln Val Thr Val Ser Ser
            115                 120
```

```
<210> SEQ ID NO 26
<211> LENGTH: 122
<212> TYPE: PRT
<213> ORGANISM: Lamos pacos

<400> SEQUENCE: 26

Met Ala Gln Val Gln Leu Val Glu Ser Gly Gly Gly Leu Val Arg Pro
1               5                   10                  15

Gly Gly Ser Leu Thr Leu Ser Cys Ala Ala Ser Gly Phe Thr Phe Ser
                20                  25                  30

Ser Tyr Gly Leu Ser Trp Val Arg Val Gln Pro Gly Lys Gly Leu Glu
            35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
                100                 105                 110
```

Ser Gln Gly Thr Gln Val Thr Val Ser Ser
        115                 120

<210> SEQ ID NO 27
<211> LENGTH: 122
<212> TYPE: PRT
<213> ORGANISM: Lamos pacos

<400> SEQUENCE: 27

Met Ala Asp Val Gln Leu Gln Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Val Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120

<210> SEQ ID NO 28
<211> LENGTH: 127
<212> TYPE: PRT
<213> ORGANISM: Lamos pacos

<400> SEQUENCE: 28

Met Ala Gln Val Gln Leu Gln Glu Ser Gly Gly Gly Leu Val Arg Pro
1               5                   10                  15

Gly Gly Ser Leu Thr Leu Ser Cys Ala Ala Ser Gly Phe Thr Pro Arg
            20                  25                  30

Gly Phe Ala Ile Gly Trp Phe Arg Gln Ala Pro Gly Lys Glu Arg Glu
        35                  40                  45

Gly Val Ser Cys Ile Ser Thr Thr Gly Ala Ile Thr Tyr Tyr Ala Asp
    50                  55                  60

Ser Ala Lys Gly Arg Phe Thr Ile Ser Arg Asp Asn Ala Lys Asn Thr
65                  70                  75                  80

Val Tyr Leu Gln Met Asn Asn Leu Lys Pro Asp Asp Thr Ala Val Tyr
                85                  90                  95

Tyr Cys Ala Ser Asp Asn Gln Cys Gly Ser Ala Trp Asn Arg His Arg
            100                 105                 110

Lys Tyr Asp Tyr Trp Gly Gln Gly Thr Gln Val Thr Val Ser Ser
        115                 120                 125

<210> SEQ ID NO 29
<211> LENGTH: 131
<212> TYPE: PRT
<213> ORGANISM: Lamos pacos

<400> SEQUENCE: 29

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Arg Thr Phe Pro
            20                  25                  30

Gly Pro Asn Met Ala Trp Phe Arg Gly Gly Pro Gly Gln Glu Arg Glu
        35                  40                  45

Phe Val Ala Ala Ile Thr Ser Arg Asp Ser Lys Thr Tyr Tyr Ala Asp
    50                  55                  60

Ser Ala Lys Gly Arg Phe Thr Ile Ser Arg Asp Asn Ala Lys Arg Thr
65                  70                  75                  80

Val Tyr Leu Gln Met Asn Asn Leu Lys Pro Glu Asp Thr Ala Val Tyr
                85                  90                  95

Tyr Cys Val Ala Leu Arg Phe Ile Gly Gly Val Cys Pro Lys Val Val
            100                 105                 110

Leu Thr Gln Arg Pro Ser Asp Tyr Arg Gly Gln Gly Thr Gln Val Thr
            115                 120                 125

Val Ser Ser
        130

<210> SEQ ID NO 30
<211> LENGTH: 122
<212> TYPE: PRT
<213> ORGANISM: Lamos pacos

<400> SEQUENCE: 30

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
            115                 120

<210> SEQ ID NO 31
<211> LENGTH: 130
<212> TYPE: PRT
<213> ORGANISM: Lamos pacos

<400> SEQUENCE: 31

Met Ala Gln Val Gln Leu Val Glu Ser Gly Gly Gly Leu Val Gln Pro
1               5                   10                  15

Gly Gly Ser Leu Arg Leu Ser Cys Asp Ala Ser Gly Pro Asn Phe Asp
            20                  25                  30

Tyr Tyr Thr Ile Gly Trp Phe Arg Glu Ala Pro Gly Lys Glu Arg Glu
        35                  40                  45

Gly Val Ser Cys Ile Thr Ile Ser Thr Gly Asp Ala Asn Tyr Ala Asp
    50                  55                  60

Ser Val Lys Ala Arg Phe Thr Thr Ser Arg Asp Ser Ala Lys Asn Thr
65                  70                  75                  80

Val Phe Leu Gln Met Ser Asn Leu Thr Pro Asp Asp Thr Gly Val Tyr
                85                  90                  95

Tyr Cys Ala Ala Asp Lys Asn Tyr Tyr Cys Ser Thr Ser Ala Phe Pro
            100                 105                 110

Arg Tyr Asn Leu Tyr Asp Tyr Trp Gly Gln Gly Thr Gln Val Thr Val
        115                 120                 125

Ser Ser
    130

<210> SEQ ID NO 32
<211> LENGTH: 127
<212> TYPE: PRT
<213> ORGANISM: Lamos pacos

<400> SEQUENCE: 32

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Pro Arg
            20                  25                  30

Gly Phe Ala Ile Gly Trp Phe Arg Gln Ala Pro Gly Lys Glu Arg Glu
        35                  40                  45

Gly Val Ser Cys Ile Ser Thr Thr Gly Ala Ile Thr Tyr Tyr Ala Asn
    50                  55                  60

Ser Val Lys Gly Arg Phe Thr Ile Ser Arg Asp Asn Ala Lys Asn Thr
65                  70                  75                  80

Val Tyr Leu Gln Met Asn Asn Leu Lys Pro Asp Asp Thr Ala Val Tyr
                85                  90                  95

Tyr Cys Ala Ser Asp Asn Gln Cys Gly Ser Ala Trp Asn Arg His Arg
            100                 105                 110

Lys Tyr Asp Tyr Trp Gly Gln Gly Thr Gln Val Thr Val Ser Ser
        115                 120                 125

<210> SEQ ID NO 33
<211> LENGTH: 122
<212> TYPE: PRT
<213> ORGANISM: Lamos pacos

<400> SEQUENCE: 33

Met Ala Gln Val Gln Leu Val Glu Ser Gly Gly Gly Leu Val Arg Pro
1               5                   10                  15

Gly Gly Ser Leu Thr Leu Ser Cys Ala Ala Ser Gly Phe Thr Phe Ser
            20                  25                  30

Ser Tyr Gly Leu Ser Trp Val Arg Pro Gln Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120

<210> SEQ ID NO 34
<211> LENGTH: 122

```
<212> TYPE: PRT
<213> ORGANISM: Lamos pacos

<400> SEQUENCE: 34

Met Ala Gln Val Gln Leu Val Glu Ser Gly Gly Met Val Gln Pro
1               5                   10                  15

Gly Gly Ser Leu Arg Leu Ser Cys Ala Ala Ser Arg Phe Thr Phe Ser
            20                  25                  30

Asn Tyr Ala Met Ser Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120

<210> SEQ ID NO 35
<211> LENGTH: 122
<212> TYPE: PRT
<213> ORGANISM: Lamos pacos

<400> SEQUENCE: 35

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ala
            20                  25                  30

Lys Tyr Ala Met Thr Trp Val Arg Gln Ala Pro Gly Lys Gly Leu Glu
        35                  40                  45

Trp Val Ser Asp Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120

<210> SEQ ID NO 36
<211> LENGTH: 122
<212> TYPE: PRT
<213> ORGANISM: Lamos pacos

<400> SEQUENCE: 36

Met Ala Asp Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Asp
            20                  25                  30

Asp Tyr Gly Met Ser Trp Val Arg His Ser Pro Gly Lys Gly Leu Glu
        35                  40                  45

Trp Val Ser Asp Ile Ser Pro Ser Gly Ala Val Lys Ala Tyr Ser Asp
```

```
                     50                  55                  60
Ser Val Lys Gly Arg Phe Thr Ile Ser Arg Asp Asn Ala Lys Asn Arg
 65                  70                  75                  80

Leu Tyr Leu Gln Met Asn Ser Leu Thr Pro Glu Asp Thr Gly Glu Tyr
                     85                  90                  95

Phe Cys Thr Lys Val Gln Ser Pro Arg Thr Arg Ile Pro Ala Pro Ser
                    100                 105                 110

Ser Gln Gly Thr Gln Val Thr Val Ser Ser
                    115                 120

<210> SEQ ID NO 37
<211> LENGTH: 122
<212> TYPE: PRT
<213> ORGANISM: Lamos pacos

<400> SEQUENCE: 37

Met Ala Gln Val Gln Leu Val Glu Ser Gly Gly Gly Leu Val Gln Pro
  1               5                  10                  15

Gly Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu Glu
             35                  40                  45

Trp Val Ser Asp Ile Ser Pro Ser Gly Ala Val Lys Ala Tyr Ser Asp
         50                  55                  60

Ser Val Lys Gly Arg Phe Thr Ile Ser Arg Asp Asn Ala Lys Asn Arg
 65                  70                  75                  80

Leu Tyr Leu Gln Met Asn Ser Leu Thr Pro Glu Asp Thr Gly Glu Tyr
                     85                  90                  95

Phe Cys Thr Lys Val Gln Ser Pro Arg Thr Arg Ile Pro Ala Pro Ser
                    100                 105                 110

Ser Gln Gly Thr Gln Val Thr Val Ser Ser
                    115                 120

<210> SEQ ID NO 38
<211> LENGTH: 123
<212> TYPE: PRT
<213> ORGANISM: Lamos pacos

<400> SEQUENCE: 38

Met Ala Gln Val Gln Leu Val Glu Ser Gly Gly Gly Leu Val Gln Pro
  1               5                  10                  15

Gly Gly Ser Leu Arg Leu Ser Cys Ala Ala Ser Gly Phe Thr Phe Ser
                 20                  25                  30

Val Tyr Ala Met Ser Trp Val Arg Gln Ala Pro Gly Lys Gly Leu Glu
             35                  40                  45

Trp Val Ser Asp Ile Ser Pro Ser Gly Ala Val Lys Ala Tyr Ser Asp
         50                  55                  60

Ser Val Lys Gly Arg Phe Thr Ile Ser Arg Asp Asn Ala Lys Asn Thr
 65                  70                  75                  80

Leu Tyr Leu Arg Met Asn Ser Leu Glu Pro Asp Asp Thr Gly Val Tyr
                     85                  90                  95

Tyr Cys Val Lys Lys Thr Arg Ser Asp Gly Ile Thr Met Tyr Asp His
                    100                 105                 110

Trp Gly Gln Gly Ala Gln Val Thr Val Ser Ser
                    115                 120
```

```
<210> SEQ ID NO 39
<211> LENGTH: 122
<212> TYPE: PRT
<213> ORGANISM: Lamos pacos

<400> SEQUENCE: 39

Met Ala Gln Val Gln Leu Val Glu Ser Gly Gly Gly Leu Val Gln Pro
1               5                   10                  15

Gly Gly Ser Leu Thr Leu Ser Cys Ala Ala Ser Gly Phe Ala Phe Asp
            20                  25                  30

Asp Tyr Gly Met Asn Trp Val Arg His Ser Pro Gly Lys Gly Leu Glu
        35                  40                  45

Trp Val Ser Ala Ile Ser Pro Ser Gly Ala Val Lys Ala Tyr Ser Asp
    50                  55                  60

Ser Val Lys Gly Arg Phe Thr Ile Ser Arg Asp Asn Ala Lys Asn Arg
65                  70                  75                  80

Leu Tyr Leu Gln Met Asn Ser Leu Thr Pro Glu Asp Thr Gly Glu Tyr
                85                  90                  95

Phe Cys Thr Lys Val Gln Ser Pro Arg Thr Arg Ile Pro Ala Pro Ser
            100                 105                 110

Ser Gln Gly Thr Gln Val Thr Val Ser Ser
        115                 120

<210> SEQ ID NO 40
<211> LENGTH: 127
<212> TYPE: PRT
<213> ORGANISM: Lamos pacos

<400> SEQUENCE: 40

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Pro Arg
            20                  25                  30

Gly Phe Ala Ile Gly Trp Phe Arg Gln Ala Pro Gly Lys Glu Arg Glu
        35                  40                  45

Gly Val Ser Cys Ile Ser Thr Thr Gly Ala Ile Thr Tyr Tyr Ala Asn
    50                  55                  60

Ser Val Lys Gly Arg Phe Thr Ile Ser Arg Asp Asn Ala Lys Asn Thr
65                  70                  75                  80

Val Tyr Leu Gln Met Asn Asn Leu Lys Pro Asp Asp Thr Ala Val Tyr
                85                  90                  95

Tyr Cys Ala Ser Asp Asn Gln Cys Gly Ser Ala Trp Asn Arg His Arg
            100                 105                 110

Lys Tyr Asp Tyr Trp Gly Gln Gly Thr Gln Val Thr Val Ser Ser
        115                 120                 125

<210> SEQ ID NO 41
<211> LENGTH: 122
<212> TYPE: PRT
<213> ORGANISM: Lamos pacos

<400> SEQUENCE: 41

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ala
            20                  25                  30

Glu Tyr Ala Met Thr Trp Val Arg Gln Ala Pro Gly Lys Gly Leu Glu
        35                  40                  45
```

```
Trp Val Ser Asp Ile Ser Pro Ser Gly Ala Val Lys Ala Tyr Ser Asp
    50              55              60

Ser Val Lys Gly Arg Phe Thr Ile Ser Arg Asp Asn Ala Lys Asn Arg
65              70              75              80

Leu Tyr Leu Gln Met Asn Ser Leu Thr Pro Glu Asp Thr Gly Glu Tyr
            85              90              95

Phe Cys Thr Lys Val Gln Ser Pro Arg Thr Arg Ile Pro Ala Pro Ser
            100             105             110

Ser Gln Gly Thr Gln Val Thr Val Ser Ser
            115             120
```

DETECTION AND VISUALIZATION OF THE CELL CYCLE IN LIVING CELLS

CROSS REFERENCE TO RELATED APPLICATIONS

This application is a 35 U.S.C. 371 U.S. National Phase Entry of International Application No. PCT/EP2010/059622 filed Jul. 6, 2010, which designates the U.S., and which claims the benefit of priority of European Application No. 09008827.9 filed Jul. 6, 2009, the contents of which are each incorporated herein by reference in its entirety.

The present invention relates to a nucleic acid molecule encoding a polypeptide specifically binding to proliferating cell nuclear antigen (PCNA), said nucleic acid molecule comprising a nucleic acid sequence encoding the amino acid sequence of SEQ ID NO: 2 or an amino acid sequence deviating from SEQ ID NO: 2 by conservative substitution of one or more amino acids in position 1 to 28, 38 to 52, 63 to 98 and 115 to 122 of SEQ ID NO: 2. The present invention also relates to a vector comprising the nucleic acid molecule of the invention, a host cell comprising the nucleic acid molecule of or the vector of the invention and a method of detecting the amount and/or location of PCNA in living cells, as well as a method of screening for compounds having an effect on the cell cycle.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Antibodies are valuable tools to identify and visualize cellular structures. However, the application of naturally occurring antibodies for the detection of intracellular antigens requires permeabilization (and often fixation) of cells. Moreover, the antibody-based detection of antigens within intact cells is essentially prevented by the fact that antibodies are, by nature, designed to function in an oxidizing (extracellular) environment: the reducing environment in the cytoplasm leads to an impaired disulfide bond formation, resulting in an inefficient assembly of epitope recognizing parts of the variable light and heavy chain (Biocca et al. (1990); Cattaneo et al. (1999). In only a few cases intracellular antibodies (ICAbs) have been used to affect protein function in vivo but still little is known about their properties in living cells (Biocca et al. (1993); Biocca et al. (1990); Marasco et al. (1998); Cardinale et al. (1998); Kontermann (2004).

In an attempt to avoid the problems associated with the application of antibodies in the cytoplasm of intact cells, protein expression has in the past been studied by fusing proteins of interest to fluorescent proteins such as GFP ("GFP-tagging"). Tagging of proteins with fluorescent proteins has become an extremely popular method to study intracellular trafficking of proteins and, in combination with fluorescence photobleaching techniques, has provided unique information on protein dynamics in living cells. However, only the dynamics of chimeric proteins can be measured, whereas the authentic proteins, their posttranslational modifications as well as non-proteinaceous components of the cell cannot be assessed by the available methods. Furthermore, most of these approaches result in the aggregation of the fusion protein in the cell, i.e. in a location and/or expression which does not correspond to the natural location and/or expression of protein (Chalfie and Kain, 2005; Leonhardt et al., 1998).

In recent times, the exploration of the cell cycle and processes involved therein has gained more and more interest. Apart from the visual detection of the different phases of the cell cycle using light microscopy, commonly applied methods to study the cell cycle comprise staining of chromosomes which involves the fixation of the cells and staining of the nucleus with fluorescent dyes such as DAPI which is not useful to trace specific proteins involved in the cell cycle.

To overcome these limitations, it would be desirable to generate detectable protein binders which avoid the problems and limitations of naturally occurring antibodies and to establish their application in the living cell preferably avoiding interference with cellular processes. These binders would preferably be useful to trace the different stages of the cell cycle and specific proteins.

Accordingly, the present invention relates to a nucleic acid molecule encoding a polypeptide specifically binding to proliferating cell nuclear antigen (PCNA), said nucleic acid molecule comprising a nucleic acid sequence encoding the amino acid sequence of SEQ ID NO: 2 or an amino acid sequence deviating from SEQ ID NO: 2 by conservative substitution of one or more amino acids in position 1 to 28, 38 to 52, 63 to 98 and 115 to 122 of SEQ ID NO: 2. Examples of such polypeptides comprising conservative substitutions of one or more amino acids in one or two framework regions are represented by SEQ ID NOs: 16 and 18.

The term "nucleic acid molecule" as used interchangeably with the term "polynucleotide", in accordance with the present invention, includes DNA, such as cDNA or genomic DNA, and RNA such as mRNA. Further included are nucleic acid mimicking molecules known in the art such as synthetic or semi-synthetic derivatives of DNA or RNA and mixed polymers as long as they can be introduced and expressed in a cell. Nucleic acid molecules may contain additional non-natural or derivative nucleotide bases, as will be readily appreciated by those skilled in the art.

The term "specifically binding" in accordance with the present invention refers to the property of the polypeptides of the invention to have an affinity for specific proteins, i.e. target proteins, which is greater by the factor of at least 10, preferably at least 100, more preferably at least 1000 and most preferably at least 10000 as compared to the affinity to proteins unrelated to the target protein. The target protein of the polypeptide of the present invention is PCNA.

The term "conservative substitution" relates to replacement of one or more amino acids with another amino acid with similar chemical and physical properties such as size and charge. The term is well-known in the art and used here with the same meaning. Examples for conservative substitutions are the replacement of valine with leucine, of cysteine with serine, of glutamine with aparagine or of aspartic acid with glutamic acid or vice versa. In connection with the present invention, conservative substitutions do not or essentially not alter the properties of the polypeptide of the invention such as its binding properties and/or its behaviour within eukaryotic cells. On the example of the binding activity to PCNA, the term "essentially" denotes a binding activity of at least 70%, more preferably at least 80%, more preferably at least 90% and most preferably at least 95% as compared to that of the polypeptide of the invention not comprising amino acid substitutions. On the example of the behaviour of the polypeptide within eukaryotic cells, the term "essentially" denotes e. g. an expression and/or distribution within the cell which is comparable to that of the polypeptide of the invention not comprising amino acid substitutions.

The amino acids from position 1 to 28, 38 to 52, 63 to 98 and 115 to 122 of SEQ ID NO: 2 form the framework region of the polypeptide of the invention. In the examples, the framework regions as well as the CDR regions which are involved in the binding of PCNA, have been determined (see FIG. 1). Apart from not interfering with the binding of the polypeptide of the invention to PCNA, amino acid substitutions are to be chosen such that they do not interfere with the correct folding of the polypeptide and do not alter the three dimensional structure of the framework so that binding to PCNA is no longer possible.

From the information disclosed in the present application and from his common knowledge the skilled person knows, which amino acids can be substituted and is also aware of methods for comparing the properties of a polypeptide comprising one or more amino acid substitutions with those of the polypeptide of the invention not comprising any amino acid substitutions. Exemplary methods comprise solubility studies, aggregate formation assays, distribution analyses, binding assays and expression studies in living eukaryotic cells.

Examples of the nucleic acid of the invention encoding a polypeptide with one or more conservative substitutions on one or two framework regions are those of SEQ ID NOs: 15 and 17 encoding the polypeptides of SEQ ID NOs: 16 and 18 (see FIG. 9).

The present inventors have surprisingly found that a PCNA-binding polypeptide can be applied in living cells for the detection of the presence and/or location of PCNA in said cells. The polypeptide of the invention is derived from camelid antibodies, the general recombinant production and selection procedure of which is well known in the art (e. g. by phage display and recombinant techniques, see e.g. Hoogenboom et al. (1998); Pluckthun (1994); Verma et al. (1998)) and comprises the VHH domain of camelid heavy chain antibodies. As apparent from the appended examples, only one out of eight PCNA binding polypeptides obtained using phage display and/or the F2H assay disclosed in PCT/EP2009/000067 was able to provide the advantageous properties necessary for their application in living cells.

Antibodies specifically binding to PCNA are known in the art (Rottach et al., 2008). However, it has so far not been possible to generate antibodies which enable for the detection of PCNA in living cells without a fatal loss of function of said antibodies. Furthermore, alternative methods utilized so far rely on a fusion of a fluorescent polypeptide to PCNA and the introduction of this fusion protein into cells. This method has some major drawbacks. Inter alia, the overexpression of the fusion protein causes unwanted and unspecific aggregates which do not correspond to the amount or location of PCNA not fused to a fluorescent polypeptide. Thus, the present invention does not only overcome the drawback of this method but also for the first time provides means for detecting PCNA in living cells without interfering with the cell's normal turnover of PCNA or the function of PCNA as an essential loading platform for enzymes involved in DNA replication (Bravo R. et al., 1987).

In a preferred embodiment, the nucleic acid molecule comprises or consists of (a) the nucleic acid sequence of SEQ ID NO: 1, 15 or 17; or (b) a nucleic acid sequence degenerate with respect to the nucleic acid sequence of (a).

The term "degenerate" in accordance with the present invention refers to the degeneracy of the genetic code. A triplet code of bases designates 20 amino acids and a stop codon. Because four bases exist which are utilized to encode genetic information, triplet codons are required to produce at least 21 different codes. The possible $4^3$ possibilities for bases in triplets gives 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having a different sequence than that specified above, but still encoding the same polypeptide lie within the scope of the present invention.

In another preferred embodiment the nucleic acid molecule further comprises a nucleic acid sequence encoding a visually detectable peptidic or proteinaceous marker.

The term "visually detectable" relates to a physical or chemical property of a marker that enables for its detection using visual means. Typically, visually detectable markers can be detected since they emit radiation such as fluorescence, luminescence, phosphorescence or radioactivity.

In this embodiment, the nucleic acid of the invention encodes a polypeptide comprising a polypeptide specifically binding to PCNA according to the invention (a first polypeptide component), a visually detectable peptidic or proteinaceous marker (a second polypeptide or peptidic component) such as a fluorescent polypeptide and a linker. A polypeptide of this structure is, in connection with the present invention, also termed "fusion protein". In other words, a fusion protein according to the invention comprises two polypeptide components or one polypeptide and one peptidic or proteinaceous component and a linker.

In a more preferred embodiment said visually detectable peptidic or proteinaceous marker is a fluorescent polypeptide, wherein said fluorescent polypeptide is separated from said polypeptide specifically binding to PCNA by a linker of at least one amino acid residue.

The term "polypeptide" as used herein interchangeably with the term "protein" describes linear molecular chains of amino acids, containing more than 30 amino acids. Polypeptides according to the invention, in particular fusion proteins comprising a fluorescent polypeptide, preferably do not form oligomers. The terms "polypeptide" and "protein" also refer to naturally modified polypeptides/proteins where the modification is effected e.g. by glycosylation, acetylation, phosphorylation and similar modifications which are well known in the art.

The term "fluorescent polypeptide" or "fluorescent protein" refers to polypeptides emitting fluorescent light upon excitation at a specific wavelength. A variety of fluorescent proteins can be used in the present invention. One group of such fluorescent proteins includes Green Fluorescent Protein isolated from *Aequorea victoria* (GFP), as well as a number of GFP variants, such as cyan fluorescent protein, blue fluorescent protein, yellow fluorescent protein, etc. (Zhang et al., 2002; Zimmer, 2002). Typically, these variants or the nucleic acids encoding them share about 80%, or greater sequence identity with the amino acid sequence of SEQ ID No: 4 or the nucleic acid sequence of SEQ ID NO: 3, respectively. Color-shift GFP mutants have emission colors blue to yellow-green, increased brightness, and photostability (Tsien, 1998). One such GFP mutant, termed the Enhanced Yellow Fluorescent Protein (eYFP) (Tsien, 1998), displays an emission maximum at 529 nm. A YFP may e.g. have the amino acid sequence of SEQ ID NO: 8 or be encoded by the nucleic acid sequence of SEQ ID NO: 7. Additional GFP-based variants having modified excitation and emission spectra (Tsien et al., U.S. Patent Appn. 2002012311 3A1), enhanced fluorescence intensity and thermal tolerance (Thastrup et al., U.S. Patent Appn. 20020107362A1; Bjorn et al., U.S. Patent Appn.

20020177189A1), and chromophore formation under reduced oxygen levels (Fisher, U.S. Pat. No. 6,414,119) have also been described.

Another group of fluorescent proteins includes the fluorescent proteins isolated from anthozoans, including without limitation the red fluorescent protein isolated from *Discosoma* species of coral, DsRed (Matz et al., 1999) (see, e.g., accession number AF168419). DsRed and the other anthozoan fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP (MMDB Id: 5742). A number of mutants of the longer wavelength red fluorescent protein DsRed have also been described, and similarly, may be employed in the generation of the fusion proteins of the invention comprising fluorescent (poly)peptides. For example, recently described DsRed mutants with emission spectra shifted further to the red may be employed in the practice of the invention (Baird et al., 2000; Terskikh et al., 2000; Wiehler et al., 2001).

Monomeric versions of DsRed are e.g. mRFP, mCherry (e.g. having the amino acid sequence of SEQ ID NO: 6 or encoded by the nucleic acid sequence of SEQ ID NO: 5), mRFP1 (Campbell et al., 2002), mOrange or mPlum (Shaner et al., 2004) or TagRFP (Merzlyak et al., 2007).

Most recently, GFPs from the anthozoans *Renilla reniformis* and *Renilla kollikeri* were described (Ward et al., U.S. Patent Appn. 20030013849), which may also be used in accordance with the invention.

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with structures inferred to be similar to GFP from corals, sea pens, sea squirts, and sea anemones have been described, and may be used in the generation of the fusion proteins of the invention (for reviews, see Zhang et al., 2002; Zimmer, 2002).

Fluorescent proteins from *Anemonia majano, Zoanthus* sp., *Discosoma striata, Discosoma* sp. and *Clavularia* sp. have also been reported (Matz et al., 1999). A fluorescent protein cloned from the stony coral species, *Trachyphyllia geoffroyi*, has been reported to emit green, yellow, and red light, and to convert from green light to red light emission upon exposure to UV light (Ando et al., 2002). Recently described fluorescent proteins from sea anemones include green and orange fluorescent proteins cloned from *Anemonia sulcata* (Wiedenmann et al., 2000), a naturally enhanced green fluorescent protein cloned from the tentacles of *Heteractis magnifica* (Tu et al., 2003), a non-oligomerizing red fluorescent protein based on the chromoprotein hcriCP from *Heteractis crispa* (Gurskaya et al., 2001; Fradkov et al., 2002), a generally non fluorescent purple chromoprotein displaying weak red fluorescence cloned from *Anemonia sulcata* and a mutant thereof displaying far-red shift emission spectra (595 nm) (Lukyanov et al., 2000).

Additionally, another class of GFP-related proteins having chromophoric and fluorescent properties has been described. One such group of coral-derived proteins, the pocilloporins, exhibit a broad range of spectral and fluorescent characteristics (Dove and Hoegh-Guldberg, 1999, PCT application WO 00146233; Dove et al., 2001). Recently, the purification and crystallization of the pocilloporin Rtms5 from the reef-building coral *Montipora efflorescens* has been described (Beddoe et al., 2003). Rtms5 is deep blue in colour, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003; Bulina et al., 2002; Lukyanov et al., 2000).

Various other coral-derived chromoproteins closely related to the pocilloporins are also known (see, for example, Gurskaya et al., 2001; Lukyanov et al., 2000). Further examples of fluorescent proteins are GFP form *Renilla reniformis*, mKO from *Fungia concinna*, Azami Green from *Galaxeidae* or cOFP from *Cerianthus*.

Kredel et al. (2009) describe the fluorescent protein mRuby which is derived from *Entacmaea quadricolor*. An example of a fluorescent protein derived from bacteria is described in Shu et al. (2009).

An overview of known fluorescent proteins can be found in Shaner et al., 2007.

Any fluorescent or chromophoric protein or fluorescent or chromophoric fragment thereof may be used in accordance with the teaching of the present invention.

The term "linker" refers to the connection between the polypeptide components, or the polypeptide and the peptidic or proteinaceous components of the fusion protein of the invention. A linker in accordance with the present invention is comprised of amino acids comprising at least one amino acid residue which is located between the mentioned polypeptide components, or the polypeptide and the peptidic or proteinaceous components of the fusion protein. Such a linker may in some cases be useful, for example, to improve separate folding of the individual polypeptide components of the fusion protein of the invention or to modulate the stability of the fusion protein. Moreover, such linker residues may contain signals for transport, protease recognition sequences or signals for secondary modification. The linker may be as short as 1 amino acid residue or up to 2, 3, 4, 5, 6, 7, 8, 9, 10, 15, 20, 30, 40 or 50 residues. In particular cases, the linker may even involve up to 100 or 150 residues. It is preferred that the linker comprises between 18 and 30 amino acids, more preferably between 20 and 25 amino acids and most preferably between 22 and 24 amino acids, such as 23 amino acids.

Particularly preferred linkers comprise or consist of the amino acid sequence of SEQ ID NOs: 13 or 14.

In a more preferred embodiment, the fluorescent polypeptide is GFP, RFP or YFP, preferably encoded by the nucleic acid sequence of SEQ ID NO: 3, 5 or 7 or having the amino acid sequence of SEQ ID NO: 4, 6 or 8, or a fluorescent mutant or fragment thereof.

A "fluorescent mutant" in accordance with the present invention denotes any fluorescent protein, preferably derived from the above GFP, RFP or YFP sequences. Fluorescent mutants preferably have a sequence identity of at least 60%, more preferably at least 70%, even more preferably at least 80%, most preferably at least 85%, such as at least 90%, at least 95% or 100% to said GFP, RFP or YFP while retaining or essentially retaining their fluorescent properties.

A "fluorescent fragment" according to the invention relates to parts or fragments of the above GFP, RFP or YFP or fluorescent mutants thereof which are shortened in their sequence but still retain or essentially retain their fluorescent properties.

In connection with the present invention, the term "essentially retain" refers to the fluorescent properties of fluorescent mutants or fluorescent fragments according to the invention. In this regard, fluorescent properties essential in context with the present invention, while in principle also referring to absorption or emission spectra, relate to the brightness of a fluorescent mutant or fluorescent fragment as compared to the fluorescent polypeptide from which it is derived. Accordingly, the term "essentially retain" means that the fluorescent mutant or fluorescent fragment has at least 50%, preferably at least 60%, more preferably at least 70%, even more preferably at least 80%, yet more preferably at least 90%, most preferably at least 95% of the brightness of the fluorescent polypeptide from which it is derived.

In another more preferred embodiment the polypeptide specifically binding to PCNA is located N-terminally of said fluorescent polypeptide.

Whereas the polypeptide specifically binding to PCNA may in principle also be located C-terminally of said fluorescent polypeptide, the appended examples have been carried out with the polypeptide specifically binding to PCNA being located N-terminally of the fluorescent polypeptide. The functionality of this arrangement is demonstrated.

In a further preferred embodiment the nucleic acid molecule comprises or consists of the nucleic acid sequence of SEQ ID NO: 9, 11, 19 or 21 or encodes an amino acid sequence comprising or consisting of SEQ ID NO: 10, 12, 20 or 22.

As apparent from the appended examples, the polypeptide of the invention specifically binding to PCNA, when fused to GFP or RFP, not only exerts the desired binding activity to PCNA but can also be expressed intracellularly without interfering with the cellular processes involving PCNA. This enables for a reliable detection of the presence and/or location of PCNA in the living cell.

In a different aspect, the present invention relates to a (expression) vector comprising the nucleic acid molecule of the invention.

Preferably, the vector is a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in eukaryotic cells, such as yeast or mammalian cells, like pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for the yeast *Pichia pastoris* comprise e.g. the plasmids pAO815, pPIC9K and pPIC3.5K (all Invitrogen).

The nucleic acid molecule of the present invention referred to above may also be inserted into vectors such that a (further) translational fusion with another nucleic acid molecule is generated. The other nucleic acid molecules may encode a protein which may e.g. increase the solubility and/or facilitate the purification of the protein encoded by the nucleic acid molecule of the invention. Non-limiting examples include pET32, pET41, pET43. The vectors may also contain an additional expressible polynucleotide coding for one or more chaperones to facilitate correct protein folding. Suitable bacterial expression hosts comprise e. g. strains derived from BL21 (such as BL21(DE3), BL21(DE3)PlysS, BL21(DE3)RIL, BL21(DE3)PRARE) or Rosetta®.

For vector modification techniques, see Sambrook and Russel, 2001.

Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M 13 origins of replication.

The coding sequences according to the invention inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of transcription (e. g., translation initiation codon, promoters, enhancers, and/or insulators), internal ribosomal entry sites (IRES) (Owens et al., 2001) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operably linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically designed vectors allow the shuttling of DNA between different hosts, such as bacteria-fungal cells or bacteria-animal cells.

An expression vector according to this invention is capable of directing the replication, and the expression of the nucleic acid molecule of the invention and the polypeptide encoded thereby. The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the polynucleotides or vector into targeted cell population. Methods which are well known to those skilled in the art can be used to construct recombinant viral vectors; see, for example, the techniques described in Sambrook, 2001 and Ausubel, 2001.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Other examples for regulatory elements permitting expression in eukaryotic host cells (the more preferred embodiment) are the AOX1 or GAL1 promoter in yeast or the chicken beta-actin promoter, CAG-promoter (a combination of chicken beta-actin promoter and cytomegalovirus immediate-early enhancer), the gai10 promoter, human elongation factor 1α-promoter, CMV enhancer, CaM-kinase promoter, the Autographa californica multiple nuclear polyhedrosis virus (AcMNPV) polyhedral promoter or a globin intron in mammalian and other animal cells. Besides elements which are responsible for the initiation of transcription such regulatory elements may also comprise transcription termination signals, such as the SV40-poly-A site or the tk-poly-A site or the SV40, lacZ and AcMNPV polyhedral polyadenylation signals, downstream of the polynucleotide.

The co-transfection with a selectable marker such as dhfr, gpt, neomycin, hygromycin allows the identification and isolation of the transfected cells. The transfected nucleic acid can also be amplified to express large amounts of the encoded (poly) peptide. The dhfr (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992). Using these markers, the mammalian cells are grown in selective medium and the cells with the highest resistance are selected. Other selectable markers include G418 or neomycin resistance for eukaryotic cell culture.

Suitable expression vectors for *Drosophila* are those belonging to the pMT DES system (Invitrogen) using the *drosophila metallothionein* (MT) promoter (Bunch et al., 1988) or pAC5.1 using the *drosophila* actin 5C promoter. A vector using the GAL4-inducible USA promoter is pUAST. Yeast vectors are the pYEp vector (using a Gal10 promoter), pYX142 (single copy vector) or pYX232 (2µ plasmid using the TPI triosephosphat isomerase promoter (both Novagen)). Possible regulatory elements permitting expression in prokaryotic host cells comprise, e.g., the lac, trp or tac promoter, the lacUV5 or the trp promotor in *E. coli*. Suitable selectable markers in prokaryotic cells are tetracycline, kanamycin or ampicillin resistance genes for culturing in *E. coli* and other bacteria.

In another aspect, the present invention relates to a host cell comprising the nucleic acid molecule or the vector of the invention.

Hosts according to the invention can be single cells or non-human multi-cellular organisms. Suitable prokaryotic hosts comprise e.g. bacteria of the species *Escherichia, Streptomyces, Salmonella* or *Bacillus*. Suitable eukaryotic host cells are e.g. yeasts such as *Saccharomyces cerevisiae* or *Pichia pastoris*. Insect cells suitable for expression are e.g. *Drosophila* S2 or Spodoptera Sf9 cells.

Mammalian host cells that could be used include, human Hela, HEK293, H9 and Jurkat cells, mouse NIH3T3 and C127 cells, COS 1, COS 7 and CV1, quail QC1-3 cells, mouse L cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells) and stable, immortalized cell lines derived thereof. Alternatively, the nucleic acid molecule of the invention can be expressed in stable cell lines that contain the nucleic acid molecule of the invention, preferably the vector of the invention integrated into a chromosome.

Appropriate culture media and conditions for the above-described host cells are known in the art. Transgenic non-human animals as hosts transfected with and/or expressing the nucleic acid molecule of the present invention also lie within the scope of the invention. In a preferred embodiment, the transgenic animal is a mammal, e.g. a hamster, mouse, rat, cow, cat, pig, dog, horse, rabbit or monkey.

A method for the production of a transgenic non-human animal, for example a transgenic mouse, comprises introduction of the nucleic acid molecule or targeting vector of the present invention into a germ cell, an embryonic cell, stem cell or an egg or a cell derived therefrom. The non-human animal can be used in accordance with the invention e.g. in a method for identification of compounds, described herein below. Production of transgenic embryos and screening of those can be performed, e.g., as described by Joyner (1993). The DNA of the embryonic membranes of embryos can be analyzed using, e.g., Southern blots with an appropriate probe; see supra. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach, p. 71-112) may be used for homologous gene targeting. Other suitable ES lines include, but are not limited to, the E14 line (Hooper et al. (1987), the D3 line (Doetschman et al. (1985), the CCE line (Robertson et al. (1986), the AK-7 line (Zhuang et al. (1994). The success of generating a mouse line from ES cells bearing a specific targeted mutation depends on the pluripotence of the ES cells (i. e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born, e.g. as chimeric mice. The resultant transgenic mice are chimeric for cells having either the recombinase or reporter loci and are backcrossed and screened for the presence of the correctly targeted transgene (s) by PCR or Southern blot analysis on tail biopsy DNA of offspring so as to identify transgenic mice heterozygous for either the recombinase or reporter locus/loci.

Transgenic plants as hosts transfected with and/or expressing the nucleic acid molecule of the present invention also lie within the scope of the present invention.

The present invention also relates to a method of producing a polypeptide comprising culturing the host cell of the invention under suitable conditions and isolating the polypeptide produced. Said host cell expresses or overexpresses the polypeptide of the invention specifically binding to PCNA as described above. Accordingly, said polypeptide of the invention is produced in and isolated from the host cell.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, the skilled person is also aware that these conditions may have to be adapted to the needs of the host and the requirements of the polypeptide expressed. In case an inducible promoter controls the nucleic acid of the invention in the vector present in the host cell, expression of the polypeptide can be induced by addition of an appriopriate inducing agent. Suitable expression protocols and strategies are known to the skilled person. Depending on the cell type and its specific requirements, mammalian cell culture which is a preferred embodiment for producing the polypeptide can e.g. be carried out in RPMI or DMEM medium containing 10% (v/v) FCS, 2 mM L-glutamine and 100 U/ml penicillin/ streptomycine. The cells can be kept at 37° C. in a 5% $CO_2$, water saturated atmosphere.

Suitable expression protocols for eukaryotic cells are well known to the skilled person and can be retrieved e.g. from Sambrook, 2001.

Suitable media for insect cell culture is e.g. TNM+10% FCS or SF900 medium. Insect cells are usually grown at 27° C. as adhesion or suspension culture.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

In another aspect, the present invention relates to a polypeptide encoded by the nucleic acid molecule of the invention or produced by the method of producing a polypeptide according the invention. Preferably, the nucleic acid molecule comprises or consists of the nucleic acid sequence of SEQ ID NO: 1, 15 or 17 or a nucleic acid sequence degenerate with respect to SEQ ID NO: 1, 15 or 17.

In a preferred embodiment, the polypeptide of the invention further comprises a radioactive label. Said radioactive label may be attached to the polypeptide during or after (recombinant) expression. Radioactive labels comprised in the polypeptide of the invention enable for the rapid and immediate detection of the amount and/or location of said polypeptide in living cells.

The present invention also relates to a polypeptide encoded by the nucleic acid molecule of the invention, preferably comprising or consisting of the nucleic acid sequence of SEQ ID NO: 1, 15 or 17 or a nucleic acid sequence degenerate with respect to SEQ ID NO: 1, 15 or 17, having a fluorescent dye coupled thereto.

Fluorescent dyes in accordance with the present invention are non-proteinaceous compounds which emit fluorescent light upon excitation. Exemplary fluorescent dyes are those of the Alexa family (such as Alexa Fluor 350, 405, 430, 488, 500, 514, 532, 546, 555, 568, 594, 610, 633, 647, 660, 680, 700 and 750) the excitation and emission spectra of which cover the visible spectrum and extend into the infrared, HiLyte Fluors (AnaSpec), DyLight fluors (Pierce), the ATTO Dye series (ATTO-TEC and Sigma-Aldrich) and also less bright dyes such as rhodamine and fluorescein.

Fluorescent dyes can be, for example, covalently coupled to primary amino groups of amino acids, such as lysine, of proteins via N-Hydroxisuccinimid (NHS) ester formation.

The polypeptide of the invention labeled with a fluorescent dye can be used e. g. for the detection of PCNA in immunofluorescence and immunoblotting applications. Moreover it can be introduced into living cells using various techniques such as protein transduction (Schwarze et al., 2000) or protein delivery using for example cationic lipids (proteofection) (Dalkara et al., 2004) as will also be described further below in connection with nucleic acids.

In a different aspect, the present invention relates to a method of producing a cell containing the nucleic acid of the invention, comprising introducing the nucleic acid or the vector of the invention.

The term "introducing a nucleic acid" refers to the application of a nucleic acid to cells and its subsequent uptake and incorporation into the nucleus of said cells, preferably in the genetic information or in the form of episomes. This definition can also be applied to vectors which are specific nucleic acids.

For animal cells, the process of introducing a nucleic acid is commonly termed transfection, transformation or transduction. If viruses are used, the process is termed infection or transduction. Transfection of animal cells typically involves opening transient pores or 'holes' in the cell plasma membrane, to allow the uptake of material. In addition to electroporation, transfection can be carried out by various methods of introducing foreign DNA into a cell.

One method is transfection by calcium phosphate (see e.g. Nature Methods 2 (2005), 319-320). HEPES-buffered saline solution (HeBS) containing phosphate ions is combined with a calcium chloride solution containing the DNA to be transfected. When both solutions are combined, a fine precipitate of the positively charged calcium and the negatively charged phosphate will form, binding the DNA to be transfected on its surface. The suspension of the precipitate is then added to the cells to be transfected (usually a cell culture grown in a monolayer). Many materials have been used as carriers for transfection, among them (cationic) polymers, liposomes and nanoparticles (see e.g. U.S. Pat. No. 5,948,878, Feigner et al., 1987; Martien et al., 2008). Such methods use e.g. highly branched organic compounds, so-called dendrimers, to bind the DNA. A very efficient method is the inclusion of the DNA to be transfected in liposomes capable of fusing with the cell membrane, releasing the DNA into the cell. For eukaryotic cells, lipid-cation based transfection is more typically used, because the cells are more sensitive. Another method is the use of cationic polymers such as DEAE-dextran or polyethylenimine. The negatively charged DNA binds to the polycation and the complex is taken up by the cell via endocytosis. Transfection of genetic material can also be effected by electroporation (Neumann, E. et al., 1982, EMBO Journal, 1(7), 841-845; Potter, H., et al., 1984, PNAS, 81(22), 7161-7165).

Other methods of transfection include nucleofection, heat shock, magnetofection and transfection reagents such as Lipofectamine™, Dojindo HilyMax, Fugene, jetPEI™, Effectene or DreamFect™.

It is preferred that the introduction of the nucleic acid is stable, i.e. that it stably resides in the nucleus. If the nucleic acid introduced does not itself encode a selectable marker which provides the cell with a selection advantage, such as a resistance towards a certain herbicide, toxin or antibiotic which is present in the growth medium of the cells and if the nucleic acid introduced is not stably incorporated into the nucleus, incorporation can be promoted by co-transformation with another nucleic acid encoding such a selectable marker.

In a further aspect, the present invention relates to a method of detecting the amount and/or location of PCNA in living cells comprising (a) expressing in a eukaryotic cell the polypeptide encoded by the nucleic acid molecule of the invention further encoding a fluorescent polypeptide and a linker of at least one amino acid; and (b) detecting the fluorescence emission of the fluorescent part of said polypeptide in the cell upon excitation; wherein the location of the fluorescence emission of the fluorescent part of said polypeptide in the cell is indicative for the presence of PCNA.

The term "expressing in a eukaryotic cell" relates to the transcription and translation of the polypeptide encoded by the nucleic acid molecule of the invention further encoding a fluorescent polypeptide and a linker of at least one amino acid, i.e. the fusion protein of the invention, using appropriate expression control elements that function in the chosen cell. In this manner, the binding properties of individual fusion proteins according to the invention may be tested in cellular expression systems. To this end, a nucleic acid molecule encoding a fusion protein may be cloned into a suitable expression vector as has been described above. For this and the following aspect of the present invention, the expression system is eukaryotic, preferably mammalian.

The present method simplifies basic research on the cell cycle by providing effective and easy-to-use means to detect the presence and in particular the location of the prominent cell cycle marker PCNA. Thereby, the influence of e.g. different environmental conditions such as temperature, additives in the medium, radiation and any chemical compound on the cell cycle as well as the proliferation behaviour of different cell types can be elucidated. Furthermore, as will be described further below, the in vivo applicability of the polypeptide of the invention is useful in the screening for drugs having an influence on the cell cycle. In particular it allows to study inhibitory as well as stimulating effects of drugs by determining the ongoing of the cell cycle in real time analysing the characteristic distribution of PCNA in the different cell cycle stages. With the polypeptide of the invention also distinct cell cycle stages (G1-phase, S-phase, G2-phase or mitosis) can be distinguished by analysing the cellular distribution of the polypeptide which reflects the distribution of PCNA in the particular cell cycle stage.

The present invention also relates to a method of screening for compounds having an effect on the cell cycle comprising (a) expressing in a eukaryotic cell the polypeptide encoded by the nucleic acid molecule of the invention further comprising a nucleic acid sequence encoding a fluorescent polypeptide, wherein said fluorescent polypeptide is separated from said polypeptide specifically binding to PCNA by a linker of at least one amino acid residue; (b) contacting the cell with a test compound; and (c) detecting the fluorescence emission of the fluorescent part of said polypeptide upon excitation; wherein a change in the amount and/or location of the fluorescence emission of the fluorescent part of said polypeptide in the cell as compared to that observed in a reference eukaryotic cell expressing the polypeptide encoded by the nucleic acid molecule of the invention further comprising a nucleic acid sequence encoding a fluorescent polypeptide and not contacted with the test compound is indicative that the compound has an effect on the cell cycle.

A test compound can be but is not restricted to a compound belonging to the classes of nucleic acids, polypeptides, peptides (amino acid sequences of up to 30 amino acids), peptide aptamers, nucleic acid based aptamers, ribozymes, small molecules or antibodies or fragments thereof. The test compound can be any chemical compound.

A ribozyme (from ribonucleic acid enzyme, also called RNA enzyme or catalytic RNA) is an RNA molecule that catalyzes a chemical reaction. Many natural ribozymes catalyze either their own cleavage or the cleavage of other RNAs, but they have also been found to catalyze the aminotransferase activity of the ribosome.

Examples of well-characterized small self-cleaving RNAs are the hammerhead, hairpin, hepatitis delta virus, and in vitro-selected lead-dependent ribozymes. The organization of these small catalysts is contrasted to that of larger ribozymes, such as the group I intron.

Aptamers are oligonucleic acid or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. More specifically, aptamers can be classified as DNA or RNA aptamers or peptide aptamers. Whereas the former consist of (usually short) strands of oligonucleotides, the latter consist of a short variable peptide domain, attached at both ends to a protein scaffold.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are (poly)peptides that are designed to interfere with other protein interactions inside cells. They consist of a variable peptide loop attached at both ends to a protein scaffold. This double structural constraint greatly increases the binding affinity of the peptide aptamer to levels comparable to that of an antibody (nanomolar range). The variable loop length is typically comprised of 10 to 20 amino acids, and the scaffold may be any protein, which has good solubility properties. Currently, the bacterial protein Thioredoxin-A is the most frequently used scaffold protein, the variable loop being inserted within the reducing active site, which is a -Cys-Gly-Pro-Cys-loop in the wild protein, the two cystein lateral chains being able to form a disulfide bridge. Peptide aptamer selection can be made using different systems, but the most frequently used one is currently the yeast two-hybrid system.

An antibody can be, for example, polyclonal or monoclonal. The term "antibody" also comprises derivatives thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

The term "antibody" also includes chimeric, single chain and humanized antibodies. Antibody fragments applicable as test compounds include Fab fragments, F(ab')$_2$, Fv or scFv fragments; see, for example, Harlow and Lane (1988) and (1999), loc. cit.

A small molecule according to the present invention can be organic or inorganic and has a molecular weight of up to 2000 Daltons, preferably not more than 1000 Daltons, most preferably not more than 800 Daltons.

In a preferred embodiment, the detection is carried out using a fluorescence microscope.

A fluorescence microscope is a light microscope used to study properties of organic or inorganic substances using the phenomena of fluorescence and phosphorescence instead of, or in addition to, reflection and absorption. The specimen is illuminated with light of a specific wavelength (or wavelengths) which is absorbed by the fluorophores, causing them to emit longer wavelengths of light (of a different color than the absorbed light). The illumination light is separated from the much weaker emitted fluorescence through the use of an emission filter. Typical components of a fluorescence microscope are the light source (Xenon or Mercury arc-discharge lamp), the excitation filter, the dichroic mirror (or dichromatic beamsplitter), and the emission filter. The filters and the dichroic mirror are chosen to match the spectral excitation and emission characteristics of the fluorophore used to label the specimen. Most fluorescence microscopes in use are epi-fluorescence microscopes (i.e.: excitation and observation of the fluorescence are from above (epi) the specimen). These microscopes have become an important part in the field of biology, opening the doors for more advanced microscope designs, such as the confocal laser scanning microscope (CLSM) and the total internal reflection fluorescence microscope (TIRF). These technologies are well known to the skilled person.

The compounds identified with the present method, also called lead compounds, may be optimized to arrive at a compound which may be, for example, used in a pharmaceutical composition. Methods for the optimization of the pharmacological properties of compounds identified in screens are known in the art and comprise methods of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-activity relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 2000, 140(8): 813).

In another aspect, the present invention relates to the use of the nucleic acid of the invention, the vector of the invention, the host cell of the invention, the polypeptide of the invention or produced by the method of the invention in biomedical research or drug screening.

In this regard, the embodiments described for the method of screening for compounds having an effect on the cell cycle according to the invention as described above equally apply to the use according to the invention.

Drug screening, for example, makes use of the detection of distinct cell cycle stages like S phase, G1 phase, G2 phase or mitosis in cells expressing the polypeptide of the invention after treatment with test compounds which can be drugs. A compound can be but is not restricted to a compound belonging to the classes of e.g. nucleic acids, (poly)peptides, peptide aptamers, nucleic acid based aptamers, small molecules or antibodies or fragments thereof. The compound can be any chemical compound.

Biomedical research or drug screening preferably includes the screening/identification of compounds which block the entrance of a cell into S phase or which interfere with the progression of S phase, which can be carried out using e.g. the method of screening for compounds having an effect on the cell cycle as described above. This is of particular interest to identify potential drugs which can inhibit genome replication and therefore have a direct impact in cancer treatment by blocking cellular division.

Exemplary screening methods include contacting cells expressing the polypeptide of the invention with test compounds, e.g. in a multiwell format (96-well, 384-well or other formats), followed by fluorescent live cell microscopy and fluorescence detection as described above. Using live cell imaging and fluorescence detection, the polypeptide of the invention can be visualized in the nucleus of a cell after binding to PCNA. Thereby, endogenous PCNA can be detected at characteristic structures derived from replication sites ranging from early replicating genes (early S phase) to late replicating chromatin in late S phase. Moreover, from the distribution of the polypeptide of the invention within the nucleus it can be concluded whether the cell is in G1 phase, G2 phase or in mitosis.

For the identification of specific compounds affecting the cell cycle, the distribution and the dynamic pattern of the polypeptide of the invention can be directly correlated to the distribution of the polypeptide of the invention in reference cells not contacted with the test compound.

The figures show:

FIG. 1: Alignment Report of VHHs against PCNA after Phage Display Selection (by CH.EMBnet.org Clustal W).

(*) marks identical amino acids, (:) marks conserved amino acid substitutions, (.) marks semi-conserved amino acid substitutions FIG. 2: Selection of Intracellular Functional PCNA-Chromobodies using the F2H-Assay (A) Immobilisation of GFP-PCNA at a defined cellular structure (LacI focus within the nucleus). Coexpression of red fluorescently labeled PCNA-Chromobodies. Antigen detection is visualized by colocalisation of green (antigen) and red (chromobody) fluorescence at the defined cellular structure (B) Immobilization of PCNA-Chromobodies fused to GFP at the defined cellular structure. Coexpression of RFP-PCNA was carried out. Antigen detection is visualized by colocalisation of red (antigen) and green (chromobody) fluorescence at the defined cellular structure. The coding regions of antigen-binding PCNA-Chromobodies were determined by DNA sequencing.

Figure 3:
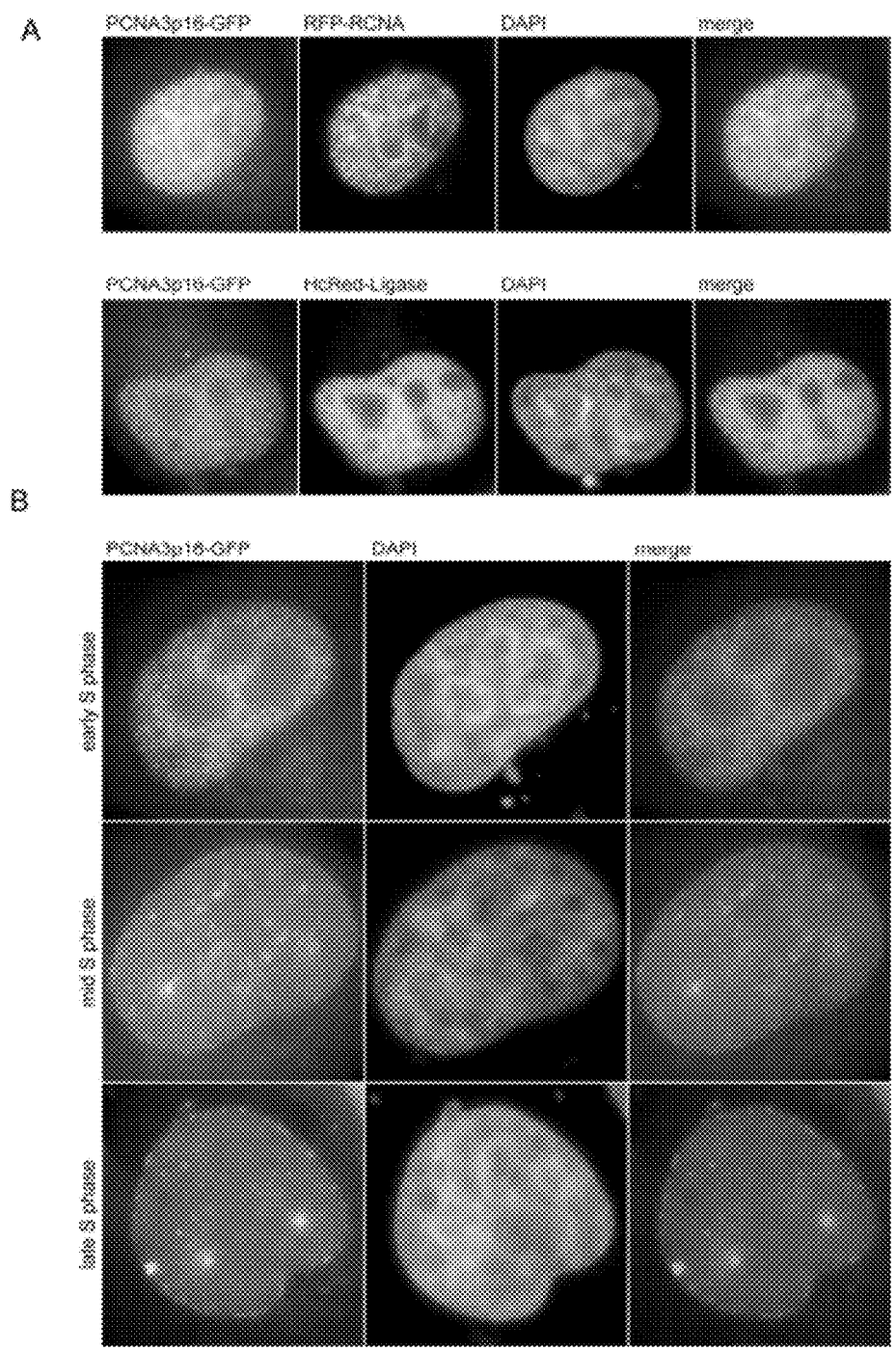

FIG. 3: Visualisation and Detection of S Phase with a PCNA-Chromobody.

Representative images of cells expressing Chromobody PCNA3p16-GFP are shown. (A) Coexpression of the PCNA-Chromobody with other fluorescent S phase markers (RFP-PCNA, HcRed-Ligase) colocalising at DNA replication sites (B) Confocal images of cells solely expressing the PCNA-Chromobody visualizing different stages of S phase.

Figure 4:
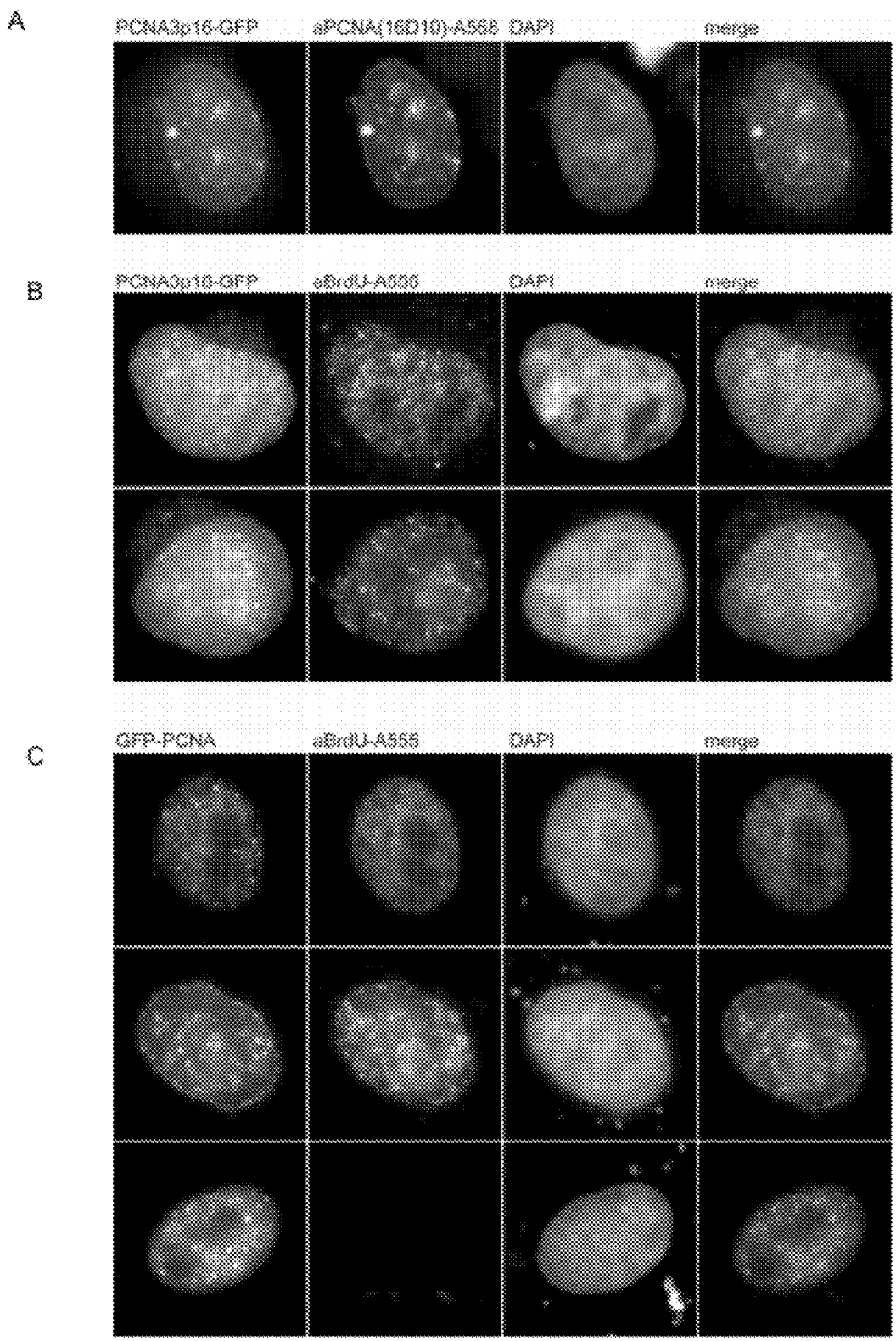

FIG. 4: S Phase Progression is not Inhibited by Expression of Chromobody PCNA3616-GFP.

(A) Conformation of the correct localization of the PCNA-Chromobody by antibody staining (immunofluorescence) using anti-PCNA antibody (16D10). Fluorescent signals of PCNA-3p16-GFP (green) colocalize with endogenous PCNA labeled with anti-PCNA(16D10) antibody-Alexa568 (red) (B) DNA-Replication sites are labeled by BrdU-incorporation during a 5 min pulse and detected with an anti-BrdU antibody-Alexa555 (aBrdU-A555; red). During a subsequent 30 min chase PCNA3p16-GFP progressed to adjacent replication foci (green). (C) Demonstration of typical mis-localization of GFP-PCNA after overexpression in living cells. Detection of replication foci with the antibody against BrdU (aBrdU-A555)

Figure 5:

FIG. 5: Representative Images of a Time Lapse Analysis of Cells Expressing Chromobody PCNA3p16-GFP Shown is the progression of a cell expressing the PCNA3p16-GFP chromobody throughout different stages of the cells cycle starting from G1 to late G2.

Figure 6:
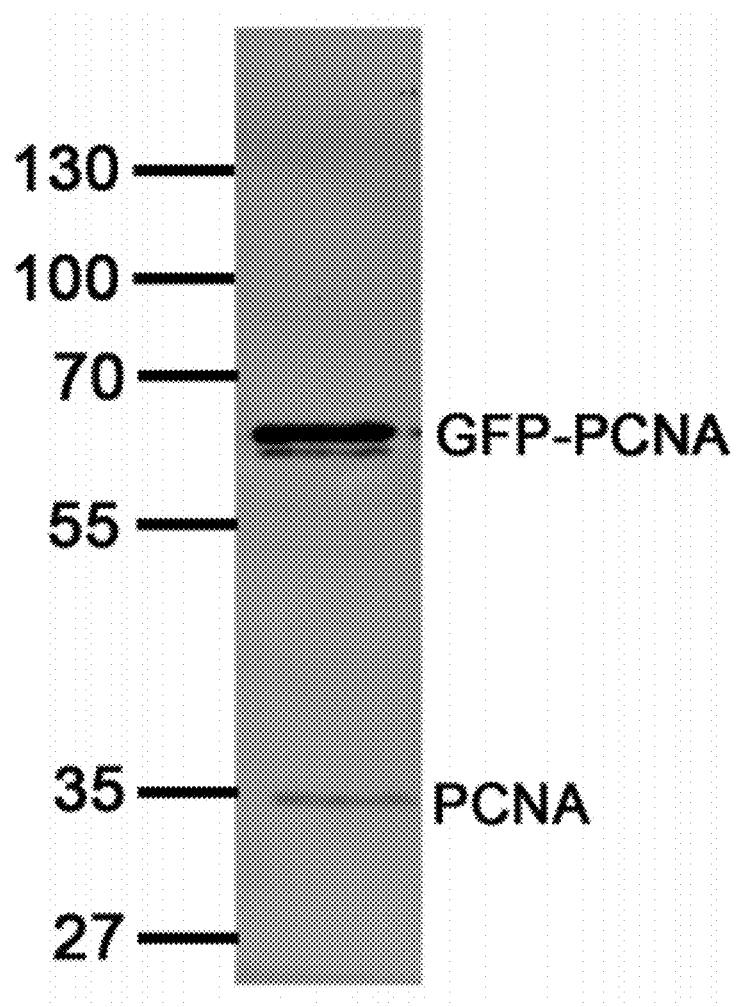

FIG. 6: Determination of Protein Levels.

Immunoblotting analysis of protein amount of transiently expressed GFP-PCNA in comparison to endogenous PCNA. Protein was detected using an anti-PCNA antibody (16D10). Relative amounts of protein was quantified using densiometrie analysis with Image J.

Figure 7:
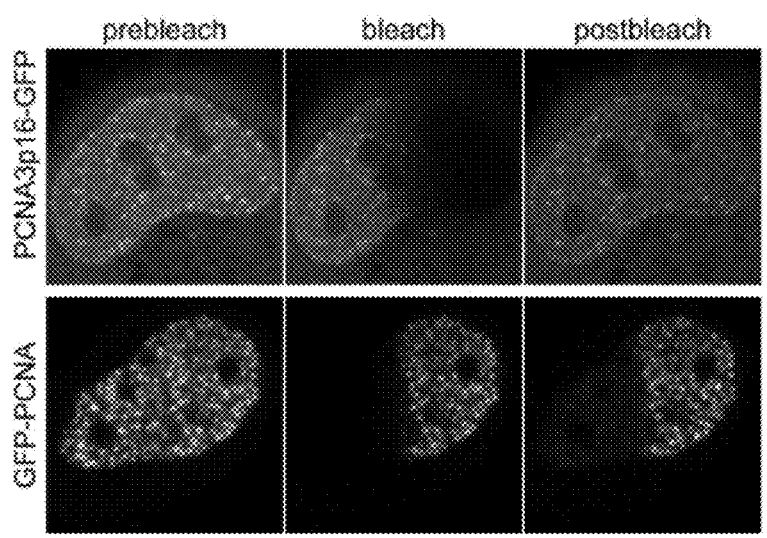
Figure 7:
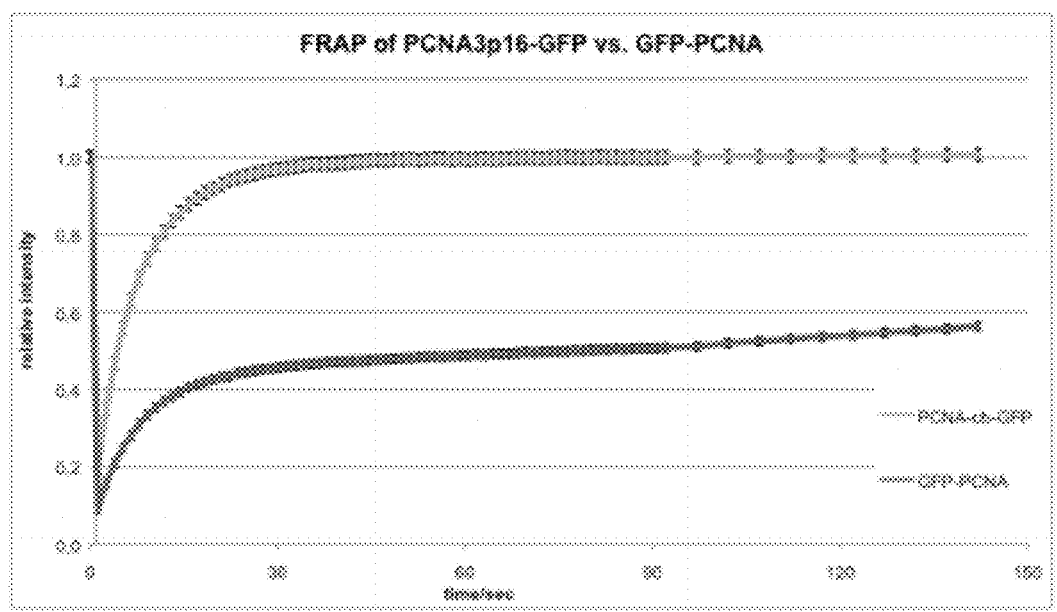

FIG. 7: Comparison of the Cellular Mobility of GFP-PCNA Versus PCNA-Chromobody with FRAP (Fluorescence Recovery after Photobleaching, FRAP) Analysis.

(A) Representative images of half nuclear FRAPs of HeLa cells either expressing Chromobody PCNA3p16-GFP of GFP-PCNA. (B) Evaluation of FRAP analysis. PCNA-Chromobody (PCNA3p16-GFP) shows a significantly faster recovery rate (~35 sec.) demonstrating a transient interaction between PCNA3p16-GFP and endogenous PCNA in living cells.

FIG. 8:

(A) Images of different clones (#5.1; #9.1; #9.6) of a HeLa cell-line stably expressing PCNA-Chromobody (PCNA3p16-GFP) shown in the GFP-channel. (B) Evaluation of a proliferation assay testing the different cell-lines. All three PCNA3p16-GFP cell-lines show homogenous expression levels, visualize endogenous replication foci and have proliferation rates comparable to a stable cell line expressing GFP-PCNA. From this we conclude that the PCNA-Chromobody shows no cellular toxicity and is therefore well suited for further studies.

FIG. 9:

Alignment of the polypeptide represented by SEQ ID NO: 2 with polypeptides comprising conservative substitutions of amino acids (SEQ ID NOs: 16 and 18). Two conservative substitutions present in both SEQ ID NO: 16 and 18 are in the framework 1 region and one conservative substitution present in SEQ ID NO: 18 is in the framework 2 region.

FIG. 10:

Representative images of cells expressing the PCNA-Chromobody(3p16) representing SEQ 2 (upper row) or polypeptides comprising conservative substitutions of amino acids representing PCNA-Chromobody representing SEQ ID NO 16 or PCNA-Chromobody SEQ ID NO 18. Shown are nuclei of cells in early S-phase (upper row), mid S-phase (middle row) or late S-phase (last row).

FIG. 11:

Mitosis assay with a HeLa cell-line stably expressing Chromobody PCNA3p16-GFP (clone 9.6). (A) a time lapse imaging of untreated cells (left) and after addition of 0.1 µg/ml Colcemid (right). Mitotic cells are visualized with PCNA-Chromobody (PCNA 3p16). Selected images of treated and untreated cells, before and after (13 h) addition of Colcemid are shown. Cells in mitosis are marked with an arrow. (B) Quantitative evaluation with automated image acquisition and computational pattern recognition. Morphological chages of cells (n~1500) were monitored in 30-min intervals. The percentage of cells in mitosis after treatment with Colcemid over a time period of 13 h is shown.

The examples illustrate the invention.

Example 1

Generation of Antibodies Binding to PCNA

Immunization of Alpaca:

One llama alpaca (Lamos pacos) was immunized with recombinant purified PCNA in GErbu adjuvant according to the following scheme: day 0, 500 µg PCNA; days 7, 14, 21, 35, 49 and 103: 125 µg PCNA. At day 110 a bleed of 100 ml was collected.

Preparation of Phage Display Library:

A total of $2 \times 10^7$ peripheral B Lymphocytes were isolated from blood (Lymphoprep™, according to manufactures instructions). After mRNA isolation and cDNA synthesis, variable domains of Alpaca heavy chain antibodies (VHH) were amplified by PCR and ligated into pHEN4c vector (Conrath et al., 2001). Transformation of ligation into TG1 cells resulted in a library of $1,5 \times 10^5$ colonies.

Panning of Phage Display Library:

To select phage displayed VHHs that bind to PCNA, 3 panning rounds against recombinant purified PCNA were performed. Positive phage clones comprising PCNA binding VHHs were detected in a solid phase ELISA. For further characterization positive clones were sequenced and the respective protein sequences were aligned with positive protein sequences derived from DNA sequences of VHH domains selected from the F2H screening (see FIG. 1)

Selection of Positive Clones Identified by the F2H Assay after 1St and 3Rd Panning Round Positive intracellular functional PCNA Chromobodies were selected using the F2H assay disclosed in PCT/EP2009/000067. Exemplary results thereof are depicted in FIG. 2. DNA sequences of positive clones from ELISA and F2H were aligned (FIG. 1). The alignment shows an enrichment of three unique protein sequences which appeared independently in both screens. Sequences of PCNA1pD5-mRFP (F2H) and PCNA3pC8-GFP (F2H) were identical to sequence PCNA1p15 (ELISA) and PCNA3pA4-mRFP (F2H) to PCNA3p10 (ELISA) and PCNA3p2 (ELISA). In subsequent in vivo analysis, however, PCNA1pD5-mRFP and PCNA3pC8-GFP did not recognize endogenous PCNA in HeLa cells. In contrast PCNA3pF6-GFP was able to bind endogenous PCNA (data not shown) and was, therefore, chosen for further characterization. In the following this claimed clone is named PCNA3p16 (having the amino acid sequence of SEQ ID NO: 2) when applied as recombinant VHH-domain and PCNA3p16-GFP (having the amino acid sequence of SEQ ID NO: 10) when used as Chromobody.

Example 2

PCNA3p16-GFP is Located at Replication Sites in HeLa Cells and S Phase Progression is not Impeded After identification of Chromobody PCNA3p16-GFP in F2H and ELISA assay, binding of the chromobody to PCNA had to be further analyzed and characterized. First, it was investigated, whether transiently expressed PCNA3p16-GFP colocalizes with RFP-PCNA or HcRedLigase, another S phase marker. To do so, HeLa cells were seeded on coverslips and transiently double transfected with expression vectors coding for RFP-PCNA or HcRed-Ligase and vector coding for PCNA-Chromobody PCNA3p16-GFP. 24 h after transfection cells were fixed in 4% PFA for 15 minutes at room temperature, permeabilized with 0,2% Triton-X-100 in PBS and the DNA was counterstained with DAPI. Slides were mounted in VectaShield and further analyzed by epifluorescence microscopy with appropriate filtersets for DAPI (D360_40X/HQ460_40M), GFP (HQ480_40X/HQ535_50M) and red fluorescent proteins (HQ565_30X/HQ620_60M) and an 63X/1.3 NA Plan Apo oil objective. As expected, RFP-PCNA as well as HcRed-Ligase localized to DNA replication sites in the nucleus of the cells. In both cases a colocalization of RFP-PCNA and HcRed-Ligase with the Chromobody PCNA3p16-GFP was detected (FIG. 3A). This result suggests that the PCNA-Chromobody localizes correctly at replication foci in cells. To rule out that correct localization of PCNA3p16-GFP is dependent on co-expression of other replication proteins, HeLa cells were transfected with PCNA3p16-GFP alone. Again a localization of PCNA3p16-GFP to replication sites was visible, indicating that PCNA3p16-GFP indeed is capable of binding endogenous PCNA at replication sites (FIG. 3B).

To confirm that PCNA3p16-GFP recognizes endogenous PCNA located at active DNA replication sites, an antibody staining against PCNA and a BrdU pulse-chase experiment were performed. For detection of endogenous PCNA with conventional antibodies cells were fixed as described above and permeabilized with 100% ice-cold methanol for 5 min. The primary anti-PCNA antibody (clone 16D10) (1:400) was detected by a secondary antibody coupled to the fluorescent dye Alexa568. To visualize active replication sites BrdU was added to the medium of proliferating cells. This nucleotide analogon is taken up by the cells and incorporated into newly synthesized DNA during S phase. After 5 minutes the BrdU containing medium is replaced by fresh medium. Cells are incubated for 30 min and subsequently fixed with 4% PFA for 15 min at room temperature. After Triton-permeabilization of cells, incorporated BrdU was visualized using a BrdU-Detection-Kit with a primary mouse anti-BrdU-antibody (1:500) and secondary anti-mouse-antibody coupled to fluorescent dye Alexa555. Microscopic analysis (as described above) of cells revealed that Chromobody PCNA3p16-GFP (green) is fully colocalizing with the endogenous PCNA protein detected by anti-PCNA antibody (16D10) (red) (FIG. 4A). This results confirms the previous result that PCNA3p16-GFP binds to endogenous PCNA.

As described above, BrdU incorporates in newly synthesized DNA, thereby labeling sites of active DNA replication in cells (red). After a 30 min chase period it was visible, that fluorescent BrdU-pattern and PCNA3p16-GFP-pattern (green) were slightly shifted. This observation suggests that endogenous PCNA had progressed to adjacent replication foci indicating that binding of PCNA3p16-GFP to endogenous PCNA did not impede S phase progression (FIG. 4B). In parallel, BrdU labeling was performed in cells transiently overexpressing GFP-PCNA. Similar to cells expressing PCNA3p16-GFP S phase progression was not inhibited in cells expressing GFP-PCNA. However, it was observed that overexpression of GFP-PCNA sometimes results in a fluorescent pattern similar to a replication pattern, although, as indicated by BrdU staining, cells were not in S-Phase.

Example 3

Live Cell Series of a HeLa Cell Expressing PCNA3p16-GFP

To confirm normal progression of HeLa cells expressing PCNA3p16-GFP through S phase a live cell series was performed. HeLa cells were seeded in ibidi μ-slide live cell chambers and transfected with expression vector coding for Chromobody PCNA3p16-GFP. 12 h after transfection cells a live cell series was started for 24 h using a PerkinElmer spinning disk confocal miscroscope equipped with a temperature controlled live cell cabinet and a Zeiss 63X/1.4 NA Plan Apo oil objective with images acquired every 15 minutes. GFP was excited with a 488 nm laser. The live cell series shows that cells progress through S phase (FIG. 5).

Example 4

Overexpression of GFP-PCNA Compared to Endogenous PCNA Protein Level in HeLa Cells To compare the level of overexpressed GFP-PCNA to endogenous PCNA level $3 \times 10^5$ HeLa cells were transiently transfected with a plasmid coding for GFP-PCNA. 20 h after transfection, transfection efficiency was determined and cell lysate prepared. Cell lysate was separated by SDS-PAGE and further analyzed by Immunoblot using anti-PCNA antibody (16D10). Quantification of immunoblot signal by ImageJ revealed that GFP-PCNA was overexpressed 15 times compared to endogenous PCNA levels. However, since only 25% of cells were transfected the quantified value was multiplied by four resulting in a 60 times higher protein level of GFP-PCNA (FIG. 6).

Example 5

FRAP Measurements of PCNA3p16-GFP Reveal a Transient, but Distinct Binding of the PCNA-Chromobody to Replication Foci For the characterization of the binding affinity of Chromobody PCNA3p16-GFP to endogenous PCNA FRAP (fluorescence recovery after photobleaching) analysis was performed. Cells were grown and transfected in ibidi μ-slides with indicated expression constructs. For FRAP analysis a Leica SP5 confocal microscope equipped with an 63X/1.4 NA Plan Apo oil objective was used. 10 pre-bleach images with a time interval of 1.3 sec were acquired. Then a maximum intensity laser pulse (488 nm) was applied to bleach a rectangular ROI (region of interest; typically half the area of the nucleus). To monitor the fluorescent recovery in the bleached area 70 images with a time interval of 1.3 sec and subsequent 10 images with a time interval of 5 sec were acquired FIG. 7A shows representative images of half nuclear FRAPs of HeLa cells either expressing Chromobody PCNA3p16-GFP (PCNA-cb-GFP) or GFP-PCNA. Statistical evaluation of FRAP measurements of several cells showed a significant faster recovery rate (~35 sec.) of Chromobody PCNA3p16-GFP compared to GFP-PCNA. This demonstrates a transient interaction between PCNA-Chromobody and endogenous PCNA in living cells. The transient nature of this interaction is most probably the reason that the function of endogenous PCNA is not disturbed or impeded by the binding of PCNA3p16-GFP. However, the binding is still specific enough to enable the visualization of the endogenous PCNA protein at replication foci throughout S phase inside living cells (FIG. 7B).

Example 6

Figure 8:
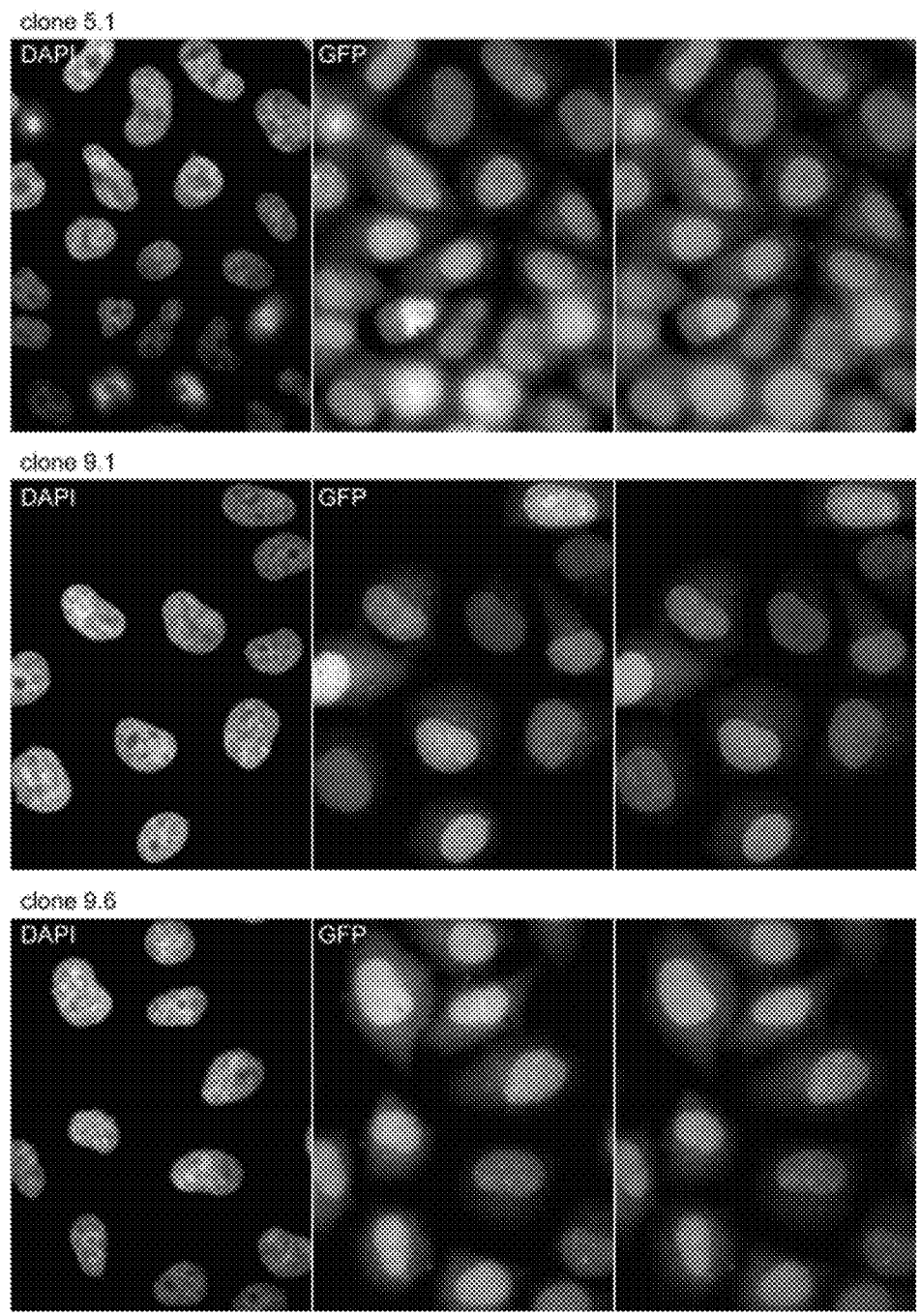
Figure 8:
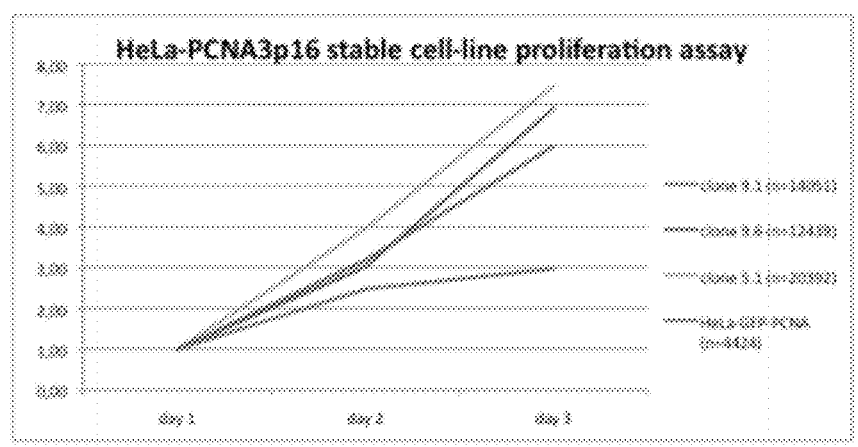

Generation and Proliferation Analysis of 3 Stable HeLa Cell-Lines Expressing PCNA3p16-GFP Transient overexpression of proteins in cells often results in inhomogeneous expression levels. Therefore, HeLa cell lines stably expressing PCNA3p16-GFP were generated. HeLa cells were seeded at very low density (1% confluence) and transfected with PCNA3p16-GFP expression vectors. 2 days after transfection, cells were cultured in medium containing G418 to select transfected cells. After several days cells expressing PCNA3p16-GFP were observed to form colonies. Colonies with homogenous and appropriate expression levels for the detection of replication patterns (i. e. expression levels enabling both for the detection of PCNA3p16-GFP and for a spatial resolution of focal structures) were chosen for further subcloning. Finally, three clones 5.1, 9.1 and 9.6 were selected (FIG. 8A).

Proliferation behaviour of all three stable cell lines was analyzed in a proliferation assay and compared to proliferation of cells stably expressing GFP-PCNA. Cells were seeded in a 6-well plate and after 1, 2 and 3 days images were acquired using an INCell Analyzer 1000 (GE Healthcare) equipped with an 10X/0.45 NA Plan Apo air objective. Cells were counted by INCell workstation, an automated image evaluation and quantification program. Clones 5.1 and 9.6 stably expressing PCNA3p16-GFP had very comparable proliferation rates to HeLa cell-line stably expressing GFP-PCNA. Cells of Clone 9.1 proliferated about 50% slower than cells expressing GFP-PCNA (FIG. 8B) However, all three PCNA3p16-GFP cell-lines show homogenous expression levels and visualize the endogenous replication foci. They are, therefore, well suited for further studies.

Example 7

Conservative Substitutions in the Framework Regions do not Impede Functionality of the Polypeptide After identification of a PCNA specific Chromobody PCNA3p16-GFP (SEQ ID NO 2), additional sequence data analysis of the PCNA-Chromobody library was performed to screen for binder sequences comprising conservative substitutions in the framework regions but not in the complementarity determining regions (CDRs) which are known to be responsible for antigen binding. Two binding sequences (amino acid sequences SEQ ID NO: 16 and SEQ ID NO: 18, see FIG. 9) were selected to be tested for PCNA binding in living cells.

To do so, HeLa cells were seeded on coverslips and transiently transfected with expression vectors coding for a variant PCNA-Chromobody of SEQ ID NO: 16 and fused to GFP or a variant PCNA-Chromobody of SEQ ID NO 18 and fused to GFP. 24 h after transfection cells were fixed in 4% PFA for 15 minutes at room temperature, permeabilized with 0,2% Triton-X-100 in PBS and the DNA was counterstained with DAPI. Slides were mounted in VectaShield and further analyzed by epifluorescence microscopy with appropriate filtersets for DAPI (D360_40X/HQ460_40M) and GFP (HQ480_40X/HQ535_50M) and an 63X/1.3 NA Plan Apo oil objective.

Figure 10:
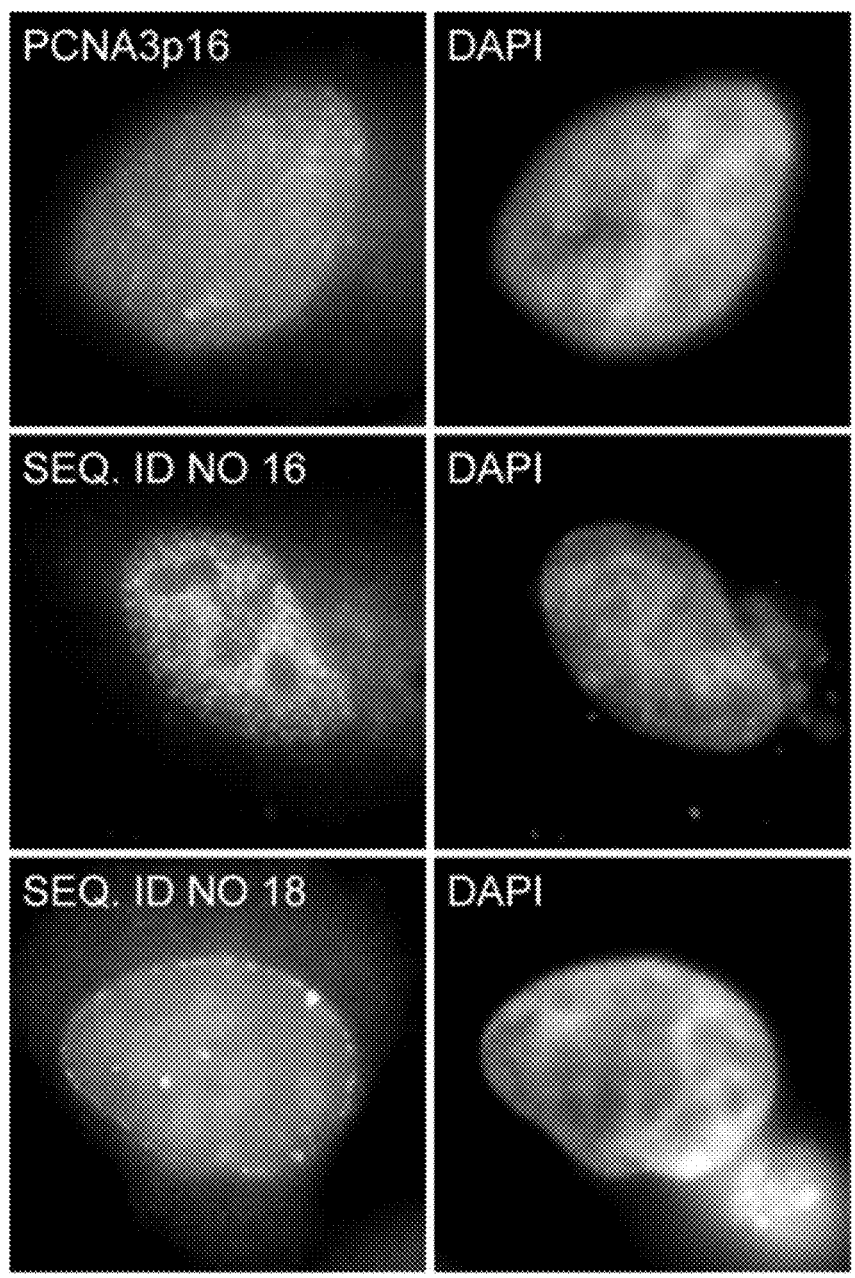

Both Chromobodies recognize PCNA and localize correctly at replication foci in cells. (see FIG. 10). From this it can be concluded that conservative mutations in the framework do not interfere with the antigen binding capacity of the corresponding chromobodies.

Example 8

Figure 11:
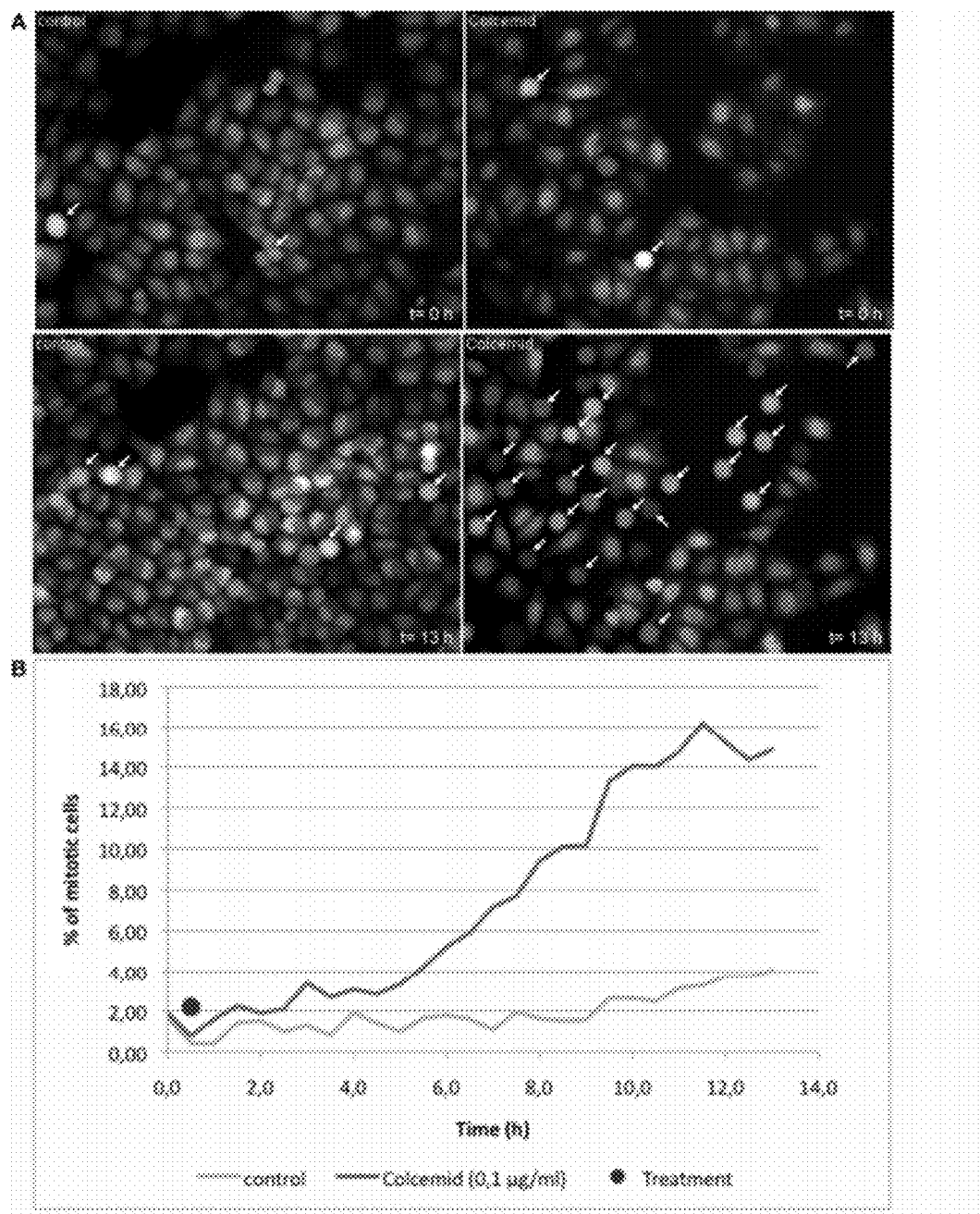

Drug Screening Using the Nucleic Acid of the Invention on the Example of the Mitotic Inducer Colcemide HeLa cell-lines stably expressing PCNA3p16-GFP (clone 9.6; amino acid sequence of SEQ ID NO: 2 fused to GFP) were seeded at 50% confluency in live cell imaging chamber (ibidi µ-Slide 8 well). After incubation over night, normal growth medium (DMEM+10% FCS) was replaced with $CO_2$ adapted live-cell medium (DMEM without phenol red+10% FCS+25 mM Hepes Buffer). Subsequently the imaging slide was placed on an INCell Analyzer 1000 (GE Healthcare) high content microscope equipped with an environmental control chamber, adjusted to 37° C. and 5% $CO_2$. Images were acquired with an 20X/0.45 NA air objective using the appropriate filterset for the fluorescent protein GFP (HQ480_40X/HQ535_50M) and an exposure time of 750 ms. For the live cell imaging 15 fields of view per well were selected and a 13 hour time series started with time intervals of 30 min. After the first time point 0.1 µg/ml Colcemid was added directly to the medium of one well; control cells were left untreated (FIG. 11A). Colcemid is a mitotic inhibitor drug such as Colchicine, which depolymerises microtubules and limits microtubule formation (inactivates spindle fibre formation), thus arresting cells in metaphase.

The acquired data set was analyzed with the automated image evaluation and quantification program INCell workstation. For that a specialized protocol was designed and developed to identify the cell, the nuclei and to distinguish between cells in interphase and metaphase. The amount of mitotic cells per time point was counted and evaluated. The plotted graph in FIG. 11B shows the expected increase of mitotic cells in the colcemid treated cell population.

REFERENCES

Ando, R., H. Hama, M. Yamamoto-Nino, H. Mizuno, and A. Miyawaki. 2002. An optical marker based on the UV-induced green-to-red photoconversion of a fluorescent protein. *Proc Natl Acad Sci* USA. 99:12651-6.

Bebbington, C. R., G. Renner, S. Thomson, D. King, D. Abrams, and G. T. Yarranton. 1992. High-level expression of a recombinant antibody from myeloma cells using a glutamine synthetase gene as an amplifiable selectable marker. *Biotechnology* (N Y). 10:169-75.

Beddoe, T., M. Ling, S. Dove, O. Hoegh-Guldberg, R. J. Devenish, M. Prescott, and J. Rossjohn. 2003. The production, purification and crystallization of a pocilloporin pigment from a reef-forming coral. *Acta Crystallogr D Biol Crystallogr.* 59:597-9.

Biocca, S., Neuberger, M. S. & Cattaneo, A. Expression and targeting of intracellular antibodies in mammalian cells. *Embo J* 9, 101-108 (1990).

Biocca, S., Pierandrei-Amaldi, P. & Cattaneo, A. Intracellular expression of anti-p21 ras single chain Fv fragments inhibits meiotic maturation of xenopus oocytes. *Biochem. Biophys. Res. Commun.* 197, 422-427 (1993).

Biocca, S., Neuberger, M. S. & Cattaneo, A. Expression and targeting of intracellular antibodies in mammalian cells. *Embo J.* 9, 101-108 (1990).

Bravo R. et al., 1987, Nature, 326, p.515-517

Bulina, M. E., D. M. Chudakov, N. N. Mudrik, and K. A. Lukyanov. 2002. Interconversion of Anthozoa GFP-like fluorescent and non-fluorescent proteins by mutagenesis. *BMC Biochem.* 3:7.

*Calcium phosphate-mediated transfection of eukaryotic cells. Nature Methods* 2, 319-320 (2005).

Cardinale, A., Lener, M., Messina, S., Cattaneo, A. & Biocca, S. The mode of action of Y13-259 scFv fragment intracellularly expressed in mammalian cells. *FEBS Lett.* 439, 197-202 (1998).

Cattaneo, A. & Biocca, S. The selection of intracellular antibodies. *Trends Biotechnol.* 17, 115-121 (1999).

Chalfie M., Kain S., Green fluorescent protein: properties, applications, and protocols, Vol. 2, John Wiley and Sons, 2005 ISBN 0471736821, 9780471736820.

Conrath, K. E. et al. (2001), Antimicrob Agents Chemother., 45(10): 2807-2812.

Dalkara et al., 2004, Moelcular Therapy Vol. 9, No. 6

Doetschman et al., J. Embryol. Exp. Morph. 87:27-45 (1985)

Dove, S. G., O. Hoegh-Guldberg, and S. Ranganathan. 2001. Major colour patterns of reef-building corals are due to a family of GFP-like proteins. *Coral Reefs.* 19:197-204.

Fradkov et al., Far_red fluorescent tag for protein labeling. Biochem J. 2002, 368, 17_21.

Gurskaya, N. G., A. F. Fradkov, A. Terskikh, M. V. Matz, Y. A. Labas, V. I. Martynov, Y. G. Yanushevich, K. A. Lukyanov, and S. A. Lukyanov. 2001. GFP-like chromoproteins as a source of far-red fluorescent proteins. *FEBS Lett.* 507:16-20.

Harlow and Lane "Antibodies, A Laboratory Manual", Cold Spring Harbor Laboratory Press, 1988.

Harlow and Lane "Using Antibodies: A Laboratory Manual" Cold Spring Harbor Laboratory Press, 1999

Hoogenboom H. R. et al., 1998, Antibody phage display and its applications, Immunotechnology 4:1-20;

Hooper et al., Nature 326:292-295 (1987)),

Joyner, A. L. Ed., Gene Targeting, A Practical Approach (1993), Oxford University Press.

Kredel et al., (2009) PLoS ONE, VOl 4 (2).

Kontermann, R. E. Intrabodies as therapeutic agents. *Methods* 34, 163-170 (2004).

Leonhardt H. et al., 1998, Journal of Cellular Biochemistry, Vol 30/31 p243-249.

Lukyanov, K. A., A. F. Fradkov, N. G. Gurskaya, M. V. Matz, Y. A. Labas, A. P. Savitsky, M. L. Markelov, A. G. Zaraisky, X. Zhao, Y. Fang, W. Tan, and S. A. Lukyanov. 2000. Natural animal coloration can Be determined by a nonfluorescent green fluorescent protein homolog. *J Biol Chem.* 275:25879-82.

Marasco, W. A., Chen, S., Richardson, J. H., Ramstedt, U. & Jones, S. D. Intracellular antibodies against HIV-1 envelope protein for AIDS gene therapy. *Hum. Gene. Ther.* 9, 1627-1642 (1998).

Matz, M. V., A. F. Fradkov, Y. A. Labas, A. P. Savitsky, A. G. Zaraisky, M. L. Markelov, and S. A. Lukyanov. 1999. Fluorescent proteins from nonbioluminescent Anthozoa species. *Nat Biotechnol.* 17:969-73.

McMahon and Bradley, Cell 62:1073-1085 (1990)

Murphy, G., M. I. Cockett, R. V. Ward, and A. J. Docherty. 1991. Matrix metalloproteinase degradation of elastin, type IV collagen and proteoglycan. A quantitative comparison of the activities of 95 kDa and 72 kDa gelatinases, stromelysins-1 and -2 and punctuated metalloproteinase (PUMP). *Biochem J.* 277 (Pt 1):277-9.

Pluckthun A, 1994, *Escherichia coli producing recombinant antibodies*, Bioprocess Technol. 19:233-252.

Sambrook, J and Russell, D. Molecular Cloning: A Laboratory Manual; Cold Spring Harbor 2001.

Robertson, E. J. (1987); Teratocarcinomas and Embryonic Stem Cells: A Practical Approach.

Robertson et al., Nature 323:445-448 (1986).

Rottach et al., 2008, Hybridoma, Vol. 27, No. 2.

Schwarze et al., 2000, Trends in Cell Biology, Vol. 10.

Shaner et al., 2007, Journal of Cell Science Vol 120(24)

Shu, X et al., 2009, Science Vol 324.

Tsien, R. Y. 1998. The green fluorescent protein. *Annu Rev Biochem.* 67:509-44.

Tu, H., Q. Xiong, S. Zhen, X. Zhong, L. Peng, H. Chen, X. Jiang, W. Liu, W. Yang, J. Wei, M. Dong, W. Wu, and A. Xu. 2003. A naturally enhanced green fluorescent protein from magnificent sea anemone (*Heteractis magnifica*) and its functional analysis. *Biochem Biophys Res Commun.* 301: 879-85.

Verma R. et al, 1998, *Antibody engineering: comparision of bacterial, yeast, insect and mammalian expression systems*, J. Immunol. Methods 216:165-181

Wiedenmann, J., C. Elke, K. D. Spindler, and W. Funke. 2000. Cracks in the beta-can: fluorescent proteins from *Anemonia sulcata* (Anthozoa, Actinaria). *Proc Natl Acad Sci USA.* 97:14091-6.

Zacharias, D. A.; Violin, J. D.; Newton, A. C. and Tsien, R. (2002) Partitioning of Lipid-Modified Monomeric GFPs into Membrane Microdomains of Live Cells; Science 296: 913-16.

Zhang, J., R. E. Campbell, A. Y. Ting, and R. Y. Tsien. 2002. Creating new fluorescent probes for cell biology. *Nat Rev Mol Cell Biol.* 3:906-18.

Zhuang et al., Cell 77:875-884 (1994))

Zimmer, M. 2002. Green fluorescent protein (GFP): applications, structure, and related photophysical behavior. *Chem Rev.* 102:759-81.

The invention claimed is:

1. A synthetic nucleic acid molecule encoding a polypeptide which specifically binds to proliferating cell nuclear antigen (PCNA), said nucleic acid molecule comprising a nucleic acid sequence encoding the amino acid sequence of SEQ ID NO: 2 or an amino acid sequence deviating from SEQ ID NO: 2 by conservative substitution of 2 or 3 amino acids in position 1 to 28 and 38 to 52 of SEQ ID NO: 2.

2. The nucleic acid molecule of claim 1, which comprises
(a) the nucleic acid sequence of SEQ ID NO: 1, 15 or 17; or
(b) a nucleic acid sequence that encodes the same polypeptide as the nucleic acid sequence of (a).

3. The nucleic acid molecule of claim 1 or 2 further comprising a nucleic acid sequence encoding a visually detectable peptidic or proteinaceous marker.

4. The nucleic acid molecule of claim 3, wherein said visually detectable peptidic or proteinaceous marker is a fluorescent polypeptide, wherein said fluorescent polypeptide is separated from said polypeptide specifically binding to PCNA by a linker of at least one amino acid residue.

5. The nucleic acid molecule of claim 4, wherein said fluorescent polypeptide is GFP, RFP or YFP.

6. The nucleic acid molecule of claim 4, wherein the polypeptide specifically binding to PCNA is located N-terminally of said fluorescent polypeptide.

7. The nucleic acid molecule of claim 1 comprising the nucleic acid sequence of SEQ ID NO: 9, 11, 19 or 21 or encoding an amino acid sequence comprising SEQ ID NO: 10, 12, 20 or 22.

8. A vector comprising the nucleic acid molecule of claim 1.

9. A host cell comprising the vector of claim 8.

10. A method of producing a polypeptide encoded by the nucleic acid molecule of claim 1 comprising culturing the host cell of claim 9 under suitable conditions and isolating the polypeptide produced.

11. A vector comprising the nucleic acid molecule of claim 2.

12. A host cell comprising the vector of claim 11.

13. A vector comprising the nucleic acid molecule of claim 3.

14. A host cell comprising the vector of claim 13.

15. A method of producing a polypeptide encoded by the nucleic acid molecule of claim 3 comprising culturing a host cell comprising a vector, said vector comprising the nucleic acid molecule of claim 3.

16. The nucleic acid of claim 1, wherein the amino acid sequence deviating from SEQ ID NO: 2 is SEQ ID NO: 16 or SEQ ID NO: 18.

* * * * *